(12) United States Patent
Garg et al.

(10) Patent No.: US 12,257,312 B2
(45) Date of Patent: Mar. 25, 2025

(54) CONJUGATES COMPRISING A TEMPERATURE-RESPONSIVE POLYMER AND A LIGAND CAPABLE OF BINDING ERGOSTEROL

(71) Applicants: Hyderabad Eye Institute, Hyderabad (IN); UNIVERSITY OF BRADFORD, Bradford (GB); UNIVERSITY OF SHEFFIELD, Sheffield (GB)

(72) Inventors: Prashant Garg, Hyderabad (IN); Stephen Rimmer, Bradford (GB); Charles William Ian Douglas, Sheffield (GB)

(73) Assignees: HYDERABAD EYE INSTITUTE, Hyderabad (IN); UNIVERSITY OF BRADFORD, Bradford (GB); UNIVERSITY OF SHEFFIELD, Sheffield (GB)

( * ) Notice: Subject to any disclaimer, the term of this patent is extended or adjusted under 35 U.S.C. 154(b) by 248 days.

(21) Appl. No.: 17/055,768

(22) PCT Filed: May 17, 2019

(86) PCT No.: PCT/GB2019/051369
§ 371 (c)(1),
(2) Date: Nov. 16, 2020

(87) PCT Pub. No.: WO2019/220137
PCT Pub. Date: Nov. 21, 2019

(65) Prior Publication Data
US 2021/0228734 A1 Jul. 29, 2021

(30) Foreign Application Priority Data

May 17, 2018 (IN) ............................. 201841018524
May 18, 2018 (IN) ............................. 201841018607

(51) Int. Cl.
| | |
|---|---|
| *A61K 47/69* | (2017.01) |
| *A61K 9/06* | (2006.01) |
| *A61K 31/7048* | (2006.01) |
| *A61K 31/785* | (2006.01) |
| *A61K 38/12* | (2006.01) |
| *A61K 38/14* | (2006.01) |
| *A61K 47/58* | (2017.01) |
| *A61P 31/10* | (2006.01) |
| *C12Q 1/04* | (2006.01) |

(52) U.S. Cl.
CPC ............ *A61K 47/6903* (2017.08); *A61K 9/06* (2013.01); *A61K 31/7048* (2013.01); *A61K 31/785* (2013.01); *A61K 38/12* (2013.01); *A61K 38/14* (2013.01); *A61K 47/58* (2017.08); *A61P 31/10* (2018.01); *C12Q 1/04* (2013.01)

(58) Field of Classification Search
CPC .. A61K 47/6903; A61K 9/06; A61K 31/7048; A61K 31/785; A61K 38/12; A61K 38/14; A61K 47/58; A61P 31/10; C12Q 1/04
See application file for complete search history.

(56) References Cited

U.S. PATENT DOCUMENTS

| | | | |
|---|---|---|---|
| 2011/0268807 A1 | 11/2011 | Su et al. | |
| 2013/0216600 A1* | 8/2013 | Da Silva Ferreira .. | A01N 25/26 536/6.5 |
| 2021/0228735 A1 | 7/2021 | Garg et al. | |

FOREIGN PATENT DOCUMENTS

| | | |
|---|---|---|
| WO | 2016/005288 A1 | 1/2016 |
| WO | 2019/220136 A1 | 11/2019 |
| WO | 2019/220137 A1 | 11/2019 |

OTHER PUBLICATIONS

Plenderleith, HB-PNIPAM, RSC Adv., p. 50932 (Year: 2014).*
Zaragoza, Frontiers of Microbiology, p. 1, Aug. (Year: 2012).*
Welscher, Binding Ergosterol, p. 6393, Mar. (Year: 2008).*
Rimmer HB-PNIPAM- COOH-chain ends, Soft Matter, p. 971, Jun. (Year: 2007).*
Shepherd HBPNIPAM-van, JACS Jan. p. 1736 (Year: 2010).*
Tan PEG-AMB for improved Efficacy, PLOS ONE, p. 1 Mar. (Year: 2016).*
Ansari et al., Current Thoughts in Fungal Keratitis: Diagnosis and Treatment. Curr Fungal Infect Rep. Sep. 1, 2013;7 (3):209-218.
Doroshenko et al., Antibiotic functionalised polymers reduce bacterial biofilm and bioburden in a simulated Infection of the cornea. Biomater Sci. Jul. 24, 2018;6(8):2101-2109.
Hudson et al., Injectable in situ cross-linking hydrogels for local antifungal therapy. Biomaterials. Feb. 2010;31 (6):1444-52.
Qasim et al., Enhanced Therapeutic Efficacy of Lipophilic Amphotericin B Against Candida albicans with Amphiphilic Poly (N-isoprpylacrylamide) Nanogels. Macromolecular Research. 2014;22(10)1125-1131.
Ravichandran et al., Synthesis and evaluation of anti-fungal activities of sodium alginate-amphotericin B conjugates. Int J Biol Macromol. Mar. 2018;108:1101-1109.
Shepherd et al., Hyperbranched poly(NIPAM) polymers modified with antibiotics for the reduction of bacterial burden in infected human tissue engineered skin. Biomaterials. Jan. 2011;32(1):258-67.
Swift et al., Highly-branched poly(N-isopropyl acrylamide) functionalised with pendant Nile red and chain end vancomycin for the detection of Gram-positive bacteria. Acta Biomater. Mar. 15, 2019;87:197-206.

(Continued)

*Primary Examiner* — Sarah Alawadi
*Assistant Examiner* — Thurman Wheeler
(74) *Attorney, Agent, or Firm* — McCarter & English, LLP; Steven G. Davis; Wei Song

(57) ABSTRACT

The present invention relates to polymer conjugates. More specifically, the present invention relates to polymer conjugates capable of binding to fungi, to compositions comprising these conjugates and to the use of these conjugates for detecting the presence of fungi in a sample such as, for example, a biological sample. The present invention also provides for the use of said polymer conjugates in the treatment of a fungal infection.

13 Claims, 15 Drawing Sheets

(56) References Cited

OTHER PUBLICATIONS

International Search Report and Written Opinion for Application No. PCT/GB2019/051367, dated Aug. 14, 2019, 15 pages.
International Search Report and Written Opinion for Application No. PCT/GB2019/051369, dated Aug. 14, 2019, 17 pages.
U.S. Appl. No. 17/055,782, filed Nov. 16, 2020, now Pub. No. 2021-0228735.
Sarker et al., Highly branched polymers with polymyxin end groups responsive to Pseudomonas aeruginosa. Biomacromolecules. Jan. 10, 2011;12(1):1-5.
Shepherd et al., Binding bacteria to highly branched poly(N-isopropyl acrylamide) modified with vancomycin induces the coil-to-globule transition. J Am Chem Soc. Feb. 17, 2010;132(6):1736-7.
Teratanatorn et al., Binding of Bacteria to Poly(N-isopropylacrylamide) Modified with Vancomycin: Comparison of Behavior of Linear and Highly Branched Polymers. Biomacromolecules. Sep. 11, 2017;18(9):2887-2899.
De Lima et al., An Updated Review of Macro, Micro, and Nanostructured Hydrogels for Biomedical and Pharmaceutical Applications. Pharmaceutics. Oct. 15, 2020;12(10):970, 28 pages.

* cited by examiner e)

CONJUGATES COMPRISING A TEMPERATURE-RESPONSIVE POLYMER AND A LIGAND CAPABLE OF BINDING ERGOSTEROL

CROSS-REFERENCE TO RELATED APPLICATIONS

This application is a U.S. national stage filing, under 35 U.S.C. § 371(c), of International Application No. PCT/GB2019/051369, filed on May 17, 2019, which claims priority to Indian Patent Application No. 201841018607, filed on May 18, 2018, and Indian Patent Application No. 201841018524, filed on May 17, 2018.

INTRODUCTION

The present invention relates to polymer conjugates. More specifically, the present invention relates to polymer conjugates capable of binding to fungi, to compositions comprising these conjugates and to the use of these conjugates for detecting the presence of fungi in a sample such as, for example, a biological sample. The present invention also provides for the use of said polymer conjugates in the treatment of fungal infections.

BACKGROUND OF THE INVENTION

Fungal infections are a major cause of morbidity and mortality in both humans and animals. In humans, fungal infections are a major cause of medical complications in critically ill patients.[1] A recent study found mortality rates as high as 60% for critically ill patients infected with *Candida sp.*[2] Fungal infections are also of particular concern in immune-compromised patients suffering from conditions such as HIV and AIDS.[3]

The incidence of fungal infections in tropical climates is particularly high and represents a significant medical burden. For example, fungal or mixed infections are a growing issue in corneal infections[4] in these climates.

There is, therefore, a need for new techniques to help detect the presence of fungi in a variety of environments, including possible sites of infection. In particular, there is a need for techniques to identify the presence of fungi and differentiate them from any bacterial cells that might be present.

There is also a need for improved treatments for fungal infections that show good antifungal activity with acceptable levels of toxicity.

The present invention was devised with the foregoing in mind.

SUMMARY OF THE INVENTION

The present invention resides in the identification of novel polymer conjugates that comprise ligands capable of binding to ergosterol (a target of certain antifungal agents that resides on the surface of fungal cells). The ligands are bound to a branched temperature-responsive polymer.

Thus, according to a first aspect of the present invention there is provided a polymer conjugate, or a salt thereof, having the general formula:

wherein:
P is a branched temperature-responsive polymer comprising a plurality of functional groups, wherein one or more of said functional groups are covalently attached to a ligand capable of binding to ergosterol;
Q is a ligand capable of binding to ergosterol; and
x is the percentage of functional groups on the branched temperature-responsive polymer, P, that are attached to Q, wherein x is greater than or equal to 10%.

According to a second aspect, the present invention provides a polymer conjugate as defined herein, or a salt thereof, for use in therapy.

According to a third aspect, the present invention provides a polymer conjugate as defined herein, or a salt thereof, for use in the treatment of a fungal infection.

According to a fourth aspect of the present invention, there is provided a method of treating a fungal infection in a mammal in need of such treatment, the method comprising administering a therapeutically effective amount of a polymer conjugate as defined herein, or a salt thereof.

According to a fifth aspect of the present invention, there is provided the use of a polymer conjugate as defined herein, or a salt thereof, as defined herein in the manufacture of a medicament for use in the treatment of a fungal infection.

According to a sixth aspect of the present invention, there is provided a composition comprising/consisting essentially of/consisting of support material and a polymer conjugate as defined herein, or a salt thereof, wherein the polymer conjugate is bound to the support material.

According to a seventh aspect of the present invention, there is provided a hydrogel composition comprising/consisting essentially of/consisting of hydrogel matrix, an aqueous medium (e.g. water) and a polymer conjugate as defined herein, or a salt thereof.

According to an eighth aspect of the present invention, there is provided a contact lens comprising/consisting essentially of/consisting of a hydrogel composition as defined herein.

According to a ninth aspect of the present invention, there is provided a membrane, comprising/consisting essentially of/consisting of a hydrogel composition as defined herein.

According to a tenth aspect of the present invention, there is provided a swab comprising/consisting essentially of/consisting of a hydrogel composition as defined herein.

According to an eleventh aspect of the present invention, there is provided a wound dressing comprising/consisting essentially of/consisting of a hydrogel composition as defined herein.

According to a twelfth aspect of the present invention, there is provided a method of detecting the presence of fungi in a biological sample, the method comprising:
(i) contacting a polymer conjugate, composition, hydrogel composition, contact lens, membrane, swab or wound dressing as defined herein with the biological sample;
(ii) removing either the polymer conjugate, composition, hydrogel composition, contact lens, membrane, swab or wound dressing as defined herein from the biological sample and testing it for the presence of bound fungi.

According to a thirteenth aspect of the present invention, there is provided a method of determining the presence of a fungal infection, the method comprising:
(i) contacting a polymer conjugate, composition, hydrogel composition, contact lens, membrane, swab or wound dressing as defined herein with either a sample obtained from the suspected site of infection or with the suspected site of infection directly; and
(ii) removing the polymer conjugate, composition, hydrogel composition, contact lens, membrane, swab or wound dressing and determining whether any fungi are bound to the polymer conjugate, composition, hydrogel composition, contact lens, membrane, swab or wound dressing respectively.

According to a fourteenth aspect of the present invention, there is provided a method of diagnosing the presence of a fungal infection, the method comprising:

(i) contacting a polymer conjugate, composition, hydrogel composition, contact lens, membrane, swab or wound dressing as defined herein with either a sample obtained from the suspected site of infection or with the suspected site of infection directly;

(ii) removing the conjugate, composition, hydrogel composition, contact lens, membrane, swab or wound dressing from the sample;

(iii) determining whether any fungi are attached to the conjugate, composition, hydrogel composition, contact lens, membrane, swab or wound dressing; and (iii) optionally determining the type of fungi detected.

According to a fifteenth aspect of the present invention, there is provided the use of a polymer conjugate, composition, hydrogel composition, contact lens, membrane, swab or wound dressing as defined herein for detecting the presence of fungi in a biological sample or diagnosing a fungal infection.

DETAILED DESCRIPTION OF THE INVENTION

Definitions

Unless otherwise stated, the following terms used in the specification and claims have the following meanings set out below.

The term "temperature-responsive" is used herein to refer to polymers that undergo a temperature dependent change in hydration. The temperature at which a substantial change in polymeric hydration occurs is known as the critical solution temperature (CST). The lower critical solution temperature (LCST) is the critical temperature below which the copolymer becomes highly miscible with water and, in some cases, completely soluble. Above the LCST the co-polymer is highly dehydrated and below the LCST the copolymer is highly hydrated. The term "temperature-responsive" is also used herein to refer to monomers which, when polymerised, form temperature-responsive polymers that undergo a temperature dependent change in hydration as discussed above.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to affect such treatment for the disease. The "therapeutically effective amount" will vary depending on the compound, the disease and its severity and the age, weight, etc., of the mammal to be treated.

In this specification, the term "alkyl" includes both straight and branched chain alkyl groups.

References to salts herein refer to any suitable salt forms of the polymer conjugates, including pharmaceutically acceptable salt forms. A suitable salt form of a polymer conjugate of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The Polymer Conjugates of the Invention

The present invention relates to the preparation of polymer conjugates comprising a branched temperature-responsive polymer and one or more ligands attached to the polymer that are capable of binding to ergosterol, which is present on the surface of fungi.

Ergosterol is a protovitamin found commonly within fungi and protozoan cell membranes.[5] Fungi cannot survive without ergosterol and it provides important physiological functions.[6] It therefore offers an enticing target for antifungal pharmacophores, such as for the antifungal drug amphotericin B (Amp-B).[7] The latter provides a common clinical treatment for fungal infections.[8] Although it is regularly used to treat severe fungal infections Amp-B is inherently toxic to host tissues.[1] Recent attempts to optimise the delivery of Amp-B and minimise toxicity have included attaching the drug to nanoparticles[10], detoxifying by delivery within polymer micelles[11], improving solubility by conjugating it to PEG chain ends[12] and modifying the drug with sugar moieties.[13]

The inventors have surprisingly found that the novel polymer conjugates of the present invention can effectively bind to fungi and they exhibit low toxicity. In particular, the inventors have found that the conjugates of poly(N-isopropylacrylamide) (or PNIPAM) with the antifungal agent Amp-B bound thereto (described in the accompanying example section) exhibit low toxicity compared to Amp-B alone and retain the antifungal activity of the bound amphotericin B.

Thus, the polymer conjugates of the present invention are therefore materials suitable for selectively binding to fungi. Thus, they can be immobilised on a suitable support (such as, for example, a bead, hydrogel matrix, contact lens, swab, membrane, wound dressing etc.) and contacted with a sample to bind any fungi that are present in the sample. The presence, and optionally the identity, of the bound fungi can then be determined by conventional techniques known in the art, e.g. selective staining techniques, microscopy and histological techniques. Furthermore, the polymer conjugates of the present invention in which the ligand is an antifungal agent (e.g. Amp-B) may also be used as novel antifungal agents by virtue to the retention of the antifungal activity and the low toxicity observed with the polymer conjugates.

As indicated above, the present invention provides a polymer conjugate, or a salt thereof, having the general formula:

$$P\text{-}[Q]_x$$

wherein:
P is a branched temperature-responsive polymer comprising a plurality of functional groups, wherein one or more of said functional groups are covalently attached to a ligand capable of binding to ergosterol;
Q is a ligand capable of binding to ergosterol; and
x is the percentage of functional groups on the branched temperature-responsive polymer, P, that are attached to Q, wherein x is greater than or equal to 10%.

The ligand capable of binding to ergosterol, Q, may be any suitable ligand that can bind to ergosterol known in the art. Suitably, Q is a low molecular weight compound having a molecular weight of less than 1200 Daltons. More typically, Q will be a compound with a molecular weight of less than 1000 Daltons.

In an embodiment of the invention, Q is an antifungal agent that is capable of binding to ergosterol. In a particular embodiment, Q is amphotericin B, nystatin or natamycin. In a further embodiment, Q is amphotericin B.

It will be appreciated that the functional groups of the branched temperature-responsive polymer, P, may comprise any suitable chemical functional group that is capable of forming a covalent attachment with the ligand capable of binding to ergosterol. Suitable functional groups include amino, hydroxy, alkenyl, alkynyl, acyl, sulfonyl, sulfinyl, mercapto, azido, ester, isocyanate and/or carboxyl groups. In an embodiment, the functional groups of the branched temperature-responsive polymer, P, are selected from hydroxy, acyl, sulfonyl, sulfinyl, ester and/or carboxyl groups. In another embodiment, the functional groups of the branched temperature-responsive polymer, P, are selected from sulfonyl, ester and/or carboxyl groups. In yet another embodiment, the functional groups of the branched temperature-responsive polymer, P, are carboxyl and/or ester groups. In still a further embodiment, the functional groups of the branched temperature-responsive polymer, P, are carboxyl groups.

Moreover, it will be understood that the term "plurality of functional groups" refers to two or more functional groups.

The ligands capable of binding to ergosterol, Q, may be covalently attached to the functional groups of the branched temperature-responsive polymer, P, either directly or via any suitable linkage. In an embodiment, each ligand capable of binding to ergosterol, Q, is covalently bound directly to a functional group of the branched temperature-responsive polymer.

It will be appreciated that the functional groups of the branched temperature-responsive polymer may be located at any position of the branched temperature-responsive polymer. In an embodiment, the functional groups of a branched temperature-responsive polymer are located at, or near, (preferably at) the terminal end (terminus) of each branch of the branched temperature-responsive polymer. Thus, in an embodiment, the functional groups may be said to be "terminal functional groups".

Suitably, each ligand capable of binding to ergosterol, Q, present in the polymer conjugate is bound to (a terminus of) the branched temperature-responsive polymer, P, by the reaction of a (terminal) functional group present on the branched temperature-responsive polymer, P, with a functional group present on the ligand capable of binding to ergosterol, Q, to form one of the following linking groups:
—NR$_1$—, —O—, —C(O)—O—, —O—C(O)—, —C(O)—NR$_1$—, —NR$_1$—C(O)—, —N(R$_1$)C(O)O—, —O(O)CN(R$_1$)—, —S—, —S(O)—, —S(O)$_2$—, —S(O)$_2$—NR$_1$, —NR$_1$—S(O)$_2$— or a triazole linking group (formed by "click" chemistry), wherein R$_1$ is hydrogen or (1-4C)alkyl (e.g. methyl).

In an embodiment, each ligand capable of binding to ergosterol, Q, present in the polymer conjugate is bound to (a terminus of) the branched temperature-responsive polymer, P, by the reaction of a (terminal) functional group present on the branched temperature-responsive polymer, P, with a functional group present on the ligand capable of binding to ergosterol, Q, to form one of the following linking groups:
—C(O)—O—, —O—C(O)—, —C(O)—NR$_1$—, —NR$_1$—C(O)—, —N(R$_1$)C(O)O—, —O(O)CN(R$_1$)—, —S(O)—, —S(O)$_2$—, —S(O)$_2$—NR$_1$, —NR$_1$—S(O)$_2$— or a triazole linking group (formed by "click" chemistry), wherein R$_1$ is hydrogen or (1-4C)alkyl (e.g. methyl).

In another embodiment, each ligand capable of binding to ergosterol, Q, present in the polymer conjugate is bound to (a terminus of) the branched temperature-responsive polymer, P, by the reaction of a (terminal) functional group present on the branched temperature-responsive polymer, P, with a functional group present on the ligand capable of binding to ergosterol, Q, to form one of the following linking groups:
—C(O)—NR$_1$—, —NR$_1$—C(O)—, —S(O)$_2$—NR$_1$ or —NR$_1$—S(O)$_2$—, wherein R$_1$ is hydrogen or (1-4C)alkyl (e.g. methyl).

In an embodiment, the ligand capable of binding to ergosterol, Q, present is bound to (a terminus of) the branched temperature-responsive polymer, P, by the reaction of a (terminal) carboxyl and/or ester group present on the branched temperature-responsive polymer, P, with an amine group present on the ligand capable of binding to ergosterol, Q, to form a —C(O)—NH-linking group.

Suitable chemical techniques for forming the above linking groups are well-known in the art.

It will also be understood that for a given branched temperature-responsive polymer, P, there will be a maximum theoretical number of (terminal) functional groups available for covalent attachment to a ligand capable of binding to ergosterol, Q. In each case, the actual mean number (or percentage) of ligands capable of binding to ergosterol, Q, that are attached to the (terminal) functional groups of the branched temperature-responsive polymer, P, may be determined using any suitable means known in the art (e.g. $^1$H-NMR, UV spectroscopy and/or infrared spectroscopy).

The actual mean number of ligands capable of binding to ergosterol, Q, that are attached to the (terminal) functional groups of the branched temperature-responsive polymer, P, may therefore be expressed as a percentage (or fraction) of the maximum theoretical number of (terminal) functional groups. As described hereinabove, x defines the percentage of functional groups on the branched temperature-responsive polymer, P, that are attached to the ligand capable of binding to ergosterol, Q.

In an embodiment, x is greater than or equal to 20%. Suitably, x is greater than or equal to 30%. More suitably, x is greater than or equal to 40%. Yet more suitably, x is greater than or equal to 50%. Even more suitably, x is greater than or equal to 60%. Still more suitable, x is greater than or equal to 70%. Even further suitably, x is greater than or equal to 80%. Most suitably, x is greater than or equal to 90%.

In another embodiment, x is the percentage of functional groups on the branched temperature-responsive polymer, P, that are attached to Q, wherein x is between 20% and 99%. Suitably, x is between 30% and 99%. More suitably, x is between 40% and 99%. Even more suitably, x is between 50% and 99%. Still more suitably, x is between 60% and 99%. Even further suitably, x is between 70% and 99%. Most suitably, x is between 80% and 99%.

Thus, it will be understood that in an embodiment, at least 10% of the total (terminal) functional groups present on the branched temperature-responsive polymer, P, are attached to a ligand capable of binding to ergosterol, Q. Suitably, at least 20% of the total (terminal) functional groups present on the branched temperature-responsive polymer, P, are attached to a ligand capable of binding to ergosterol, Q. More suitably, at least 30% of the total (terminal) functional groups present on the branched temperature-responsive polymer, P, are attached to a ligand capable of binding to ergosterol, Q. Even more suitably, at least 40% of the total (terminal) functional groups present on the branched temperature-responsive polymer, P, are attached to a ligand capable of binding to ergosterol, Q. Still more suitably, at least 50% of the total (terminal) functional groups present on the branched temperature-responsive polymer, P, are attached to a ligand capable of binding to ergosterol, Q. Yet more suitably, at least 60% of the total (terminal) functional groups present on the branched temperature-responsive polymer, P, are attached to a ligand capable of binding to ergosterol, Q. Even further suitably, at least 70% of the total (terminal) functional groups present on the branched temperature-responsive polymer, P, are attached to a ligand capable of binding to ergosterol, Q. Still further suitably, at least 80% of the total (terminal) functional groups present on the branched temperature-responsive polymer, P, are attached to a ligand capable of binding to ergosterol, Q. Most suitably, at least 90% of the total (terminal) functional groups present on the branched temperature-responsive polymer, P, are attached to a ligand capable of binding to ergosterol, Q.

In an embodiment, all of the (terminal) functional groups present on the branched temperature-responsive polymer, P, are covalently attached to a ligand capable of binding to ergosterol, Q.

Furthermore, the branched temperature-responsive polymer, P, may be any suitable branched temperature-responsive polymer known in the art.

Branched polymers are commonly defined by their degree of branching (DB), together with their molar masses. The degree of branching (DB) of the branched temperature-responsive polymer is commonly approximated using the following equation:

$$DB = \text{number of branch points/number of polymer repeat units.}$$

Thus, in embodiments where the branched temperature-responsive polymer terminates in a single functional group (i.e. no bi- or multi-molecular termination is present), each functional group corresponds to a branch of the polymer. Thus, the following approximation may be used to calculate the degree of branching of the branched temperature-responsive polymers of the present invention:

$$\text{number of branch points/number of repeat units} \approx \text{the number of end groups/number of repeat units.}$$

Thus, in certain embodiments, and using the above approximations, the degree of branching (DB) of the branched temperature-responsive polymers of the present invention may said to be between 0.01 and 0.5. In other embodiments, the degree of branching (DB) of the branched temperature-responsive polymers of the present invention may be said to be between 0.01 and 0.2. In further embodiments, the degree of branching (DB) of the branched temperature-responsive polymers of the present invention may be said to be between 0.02 and 0.01. In yet further embodiments, the degree of branching (DB) of the branched temperature-responsive polymers of the present invention may be said to be between 0.03 and 0.1.

Furthermore, suitable branched temperature-responsive polymers, P, of the present invention have a lower critical solution temperature (LCST) within the range of 5° C. to 70° C. In an embodiment, the branched temperature-responsive polymer, P, has a LCST within the range of 15° C. to 40° C., or 25° C. to 35° C.

In addition to temperature-dependent changes in hydration, certain polymers of the present invention (e.g. PNI-PAM) may also undergo a full or partial de-solvation upon binding of the Q group to ergosterol present on a fungal cell. Without wishing to be bound by any particular theory, it is believed that this change in conformation results in the polymer adopting a more desolvated/globular form which in turn could lead to a further increase in the affinity of the binding to the fungal cell.

The branched temperature-responsive polymer, P, may be formed from the same temperature-responsive monomers or from a mixture of different temperature-responsive monomers that polymerise to form the temperature-responsive polymer. In an embodiment, the branched temperature-responsive polymer, P, is a graft copolymer.

In an embodiment, the branched temperature-responsive polymer, P, is formed from the polymerisation of temperature-responsive monomers selected from the group consisting of N-substituted alkyl acrylamides and N-substituted alkyl methacrylamides (such as, for example, N-isopropylacrylamide and N-isopropylmethacrylamide), N,N-di-substituted alkyl acrylamide and N,N-di-substituted alkyl methacrylamides (such as, for example, N,N- isopropylacrylamide and N,N-isopropylmethacrylamide), methyl vinyl ethers, vinyl caprolactam, PEG acrylates, and amino acids (that form temperature-responsive peptides) or mixtures thereof. In a further embodiment, P is a branched temperature-responsive polymer formed from the polymerisation of temperature-responsive monomers selected from the group consisting of N-alkyl substituted acrylamides and N-alkyl substituted methacrylamides (such as, for example, N-isopropylacrylamide and N-isopropylmethacrylamide), N,N-di-alkyl substituted acrylamides and N,N-di-alkyl substituted methacrylamides (such as, for example, N,N-isopropylacrylamide and N,N-isopropylmethacrylamide), methyl vinyl ether, vinyl caprolactam, PEG acrylates or mixtures thereof. Suitably, the alkyl groups may comprise 1 to 20 carbons, e.g. 1 to 16 carbons atoms or 1 to 10 carbon atoms.

In a further embodiment, the branched temperature-responsive polymer, P, is formed from the polymerisation of temperature-responsive monomers selected from the group consisting of N-isopropylacrylamide and N-isopropylmethacrylamide, or a mixture thereof. In a further embodiment, the branched temperature-responsive polymer, P, is formed from N-isopropylacrylamide (i.e. the polymer is poly(N-isopropylacrylamide) (PNIPAM)).

In a further embodiment, the branched temperature-responsive polymer, P, is selected from branched poly(N-isopropylacrylamide)), branched poly(vinyl methyl ether), branched poly(vinyl caprolactam) or branched poly(poly (ethylene glycol) acrylate).

In a particular embodiment, the branched temperature-responsive polymer, P, is branched poly(N-isopropylacrylamide).

In addition to the temperature responsive monomers present in the polymer, a branching agent will also need to be included to provide the required degree of branching in the polymer P. A branching agent is defined as any compound that can polymerise by addition of radicals to a vinyl functionality and contains also a group that can transfer reversibly during polymerisation in the process known as reversible addition-fragmentation chain transfer (RAFT) polymerisation; such as dithonate (—SC(=S)—; dthiocarbamate (—SC(=S)NH; xanthate (—OC(=S)S—) or trithiocarbonate (—SC(=S)S—). Any suitable branching agent known in the art will suffice. Non-limiting examples of suitable branching agents include: 4-vinylbenzyl-pyrrolecarbodithioate (VPC), vinylbenzyl-phenylcarbodithioate, vinylbenzyl imidazoledithioate, vinylbenzyl alkyldithoates and derivatives thereof. Suitably, the branching agent is selected from 4-vinylbenzyl-pyrrolecarbodithioate (VPC) or vinylbenzyl-phenylcarbodithioate. Most suitably, the branching agent is 4-vinylbenzyl-pyrrolecarbodithioate (VPC).

The molar ratio of temperature responsive monomer to branching agent may be, for example, within a range of 100:1 to 10:1, or 75:1 to 10:1, or 50:1 to 10:1, or 40:1 to 15:1, or 30:1 to 20:1 (e.g. 25:1). The molar percentage of the branching agent in the final branched temperature-responsive polymer may be 0.01% to 20%, or 1% to 10%, or 1.5% to 5%, or 2% to 4%.

Thus, it will be understood that references to a "branched" polymer, P, herein refer to a temperature-responsive polymer comprising the recited temperature responsive monomers and a proportion of a suitable branching agent as defined above.

In an embodiment, the branched temperature-responsive polymer, P, is not a hyperbranched polymer.

In an embodiment, the branched temperature-responsive polymer, P, is a temperature-responsive polymer having branches occurring at every 3 to 40 monomer units. Suitably, the branched temperature-responsive polymer, P, is a temperature-responsive polymer having branches occurring at every 3 to 35 monomer units. More suitably, the branched temperature-responsive polymer, P, is a temperature-responsive polymer having branches occurring at every 10 to 35 monomer units. Even more suitably, the branched temperature-responsive polymer, P, is a temperature-responsive polymer having branches occurring at every 15 to 35 monomer units. Most suitably, the branched temperature-responsive polymer, P, is a temperature-responsive polymer having branches occurring at every 15 to 25 monomer units.

PARTICULAR EMBODIMENTS

In a particular embodiment, the branched temperature-responsive polymer, P, is a branched poly(N-isopropylacrylamide) and the ligand capable of binding to ergosterol, Q, is amphotericin B.

In a particular group of polymer conjugates of the invention, the ligand capable of binding to ergosterol, Q, is amphotericin B and the polymer conjugate has the formula IA below:

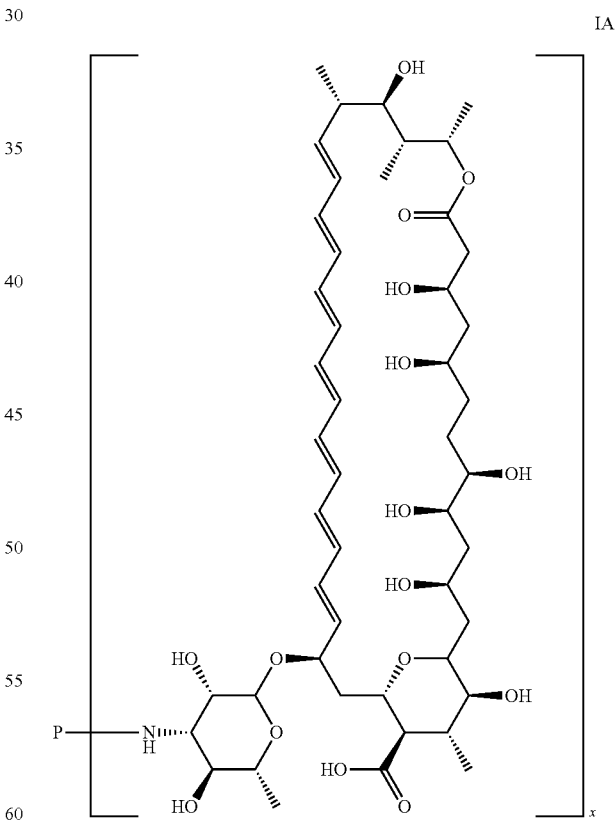

IA wherein the group in the square brackets is amphotericin B, P is the branched temperature-responsive polymer and x is the percentage of (terminal) functional groups of the branched temperature-responsive polymer that are attached to amphotericin B (e.g. greater than or equal to 50%).

In particular embodiments of the present invention, the polymer conjugate has the structural formula IA shown above, wherein:

1.1.1 P is a branched poly(N-isopropylacrylamide)), a branched poly(vinyl methyl ether), a branched poly (vinyl caprolactam) or a branched poly(poly(ethylene glycol) acrylate, wherein each of which comprises:
  a) a plurality of terminal carboxyl and/or ester groups; and
  b) a proportion of branching agents as defined above; each amphotericin B molecule is covalently attached to a terminal carboxyl and/or ester group of the branched temperature-responsive polymer, P, via its amino group, so as to form a direct linkage in the form of an amide bond; and
  at least 50% of the total terminal carboxyl and/or ester groups present on the branched temperature-responsive polymer, P, are attached to an amphotericin B molecule;

1.1.2 P is a branched poly(N-isopropylacrylamide) comprising:
  a) a plurality of terminal carboxyl groups; and
  b) a proportion of 4-vinylbenzyl-pyrrolecarbodithioate (VPC) branching agents;
  each amphotericin B molecule is covalently attached to a terminal carboxyl group of the branched temperature-responsive polymer, P, via its amino group, so as to form a direct linkage in the form of an amide bond; and
  at least 60% of the total terminal carboxyl groups present on the branched temperature-responsive polymer are attached to an amphotericin B molecule.

1.1.3 P is a branched poly(N-isopropylacrylamide) comprising:
  a) a plurality of terminal carboxyl groups; and
  b) between 0.01 and 20 mole percent of a 4-vinylbenzyl-pyrrolecarbodithioate (VPC) branching agent;
  each amphotericin B molecule is covalently attached to a terminal carboxyl group of the branched temperature-responsive polymer, P, via its amino group, so as to form a direct linkage in the form of an amide bond; and
  at least 80% of the total terminal carboxyl groups present on the branched temperature-responsive polymer are attached to an amphotericin B molecule.

Methods for forming branched temperature-responsive polymers of the present invention are known in the art. For example, suitable methods for forming branched poly(N-isopropylacrylamide) are described in Rimmer et al.[14]. The branched poly(N-isopropylacrylamide) formed by the process described in Rimmer et al.[14] possesses functional carboxy groups at the termini of the polymer branches, which can be reacted with amine groups present on suitable Q groups (e.g. amphotericin B) to form amide linkages attaching one or more Q groups to one or more termini of the branched poly(N-isopropylacrylamide).

Chemical methodologies for forming other linkages between the branched temperature-responsive polymers and the ligand(s) capable of binding to ergosterol are also well-known in the art.

Applications of the Polymer Conjugates of the Invention

The polymer conjugates of the present invention, in particular conjugates in which the ligand capable of binding to ergosterol, Q, is the antifungal agent amphotericin B, have been shown to possess antifungal activity. As a consequence, such polymer conjugates of present invention may be used as antifungal agents.

Thus, the present invention provides, a polymer conjugate as defined herein, or a salt thereof, for use in therapy.

The present invention also provides a polymer conjugate as defined herein, or a salt thereof, for use in the treatment of a fungal infection.

The present invention further provides a method of treating a fungal infection in a mammal in need of such treatment, the method comprising administering a therapeutically effective amount of a polymer conjugate as defined herein or a salt thereof.

A principal application of the polymer conjugates of the present invention relates to their utility for binding to fungal cells present in a sample, thereby enabling the presence of fungal cells in the sample to be detected. To facilitate this, the polymer conjugates of the invention may be bound to a suitable support material and then contacted with the sample concerned to bind any fungal cells present. The support material can then be removed from the sample, or vice versa, and the presence of any fungal cells bound to the polymer conjugate can be determined by a variety of conventional techniques, including staining and imaging techniques well known in the art.

Any suitable support material may be used, for example, the support may be a bead, granule or polymeric matrix. In an embodiment, the support material is a hydrogel matrix, optionally in the form of a membrane, contact lens, swab or wound dressing.

The ability of the polymer conjugates of the present invention to bind to fungal cells also makes them suitable materials for physically removing fungal cells from a sample. For example, if the polymer conjugates for the present invention are bound to a hydrogel membrane, contact lens, swab or wound dressing, they can be used to physically bind to fungal cells that they come into contact with and physically remove them from an infected site.

In view of the above, the present invention further provides a composition comprising a support and a polymer conjugate as defined herein, or a salt thereof, bound to the support.

Suitably, the polymer conjugate is covalently bound to the support.

In a further aspect, the present invention provides a hydrogel composition comprising a hydrogel polymer matrix, an aqueous medium (e.g. water) and a polymer conjugate as defined herein. Suitably, the polymer conjugate of the invention is covalently attached to hydrogel polymer matrix. More suitably, the polymer conjugate of the invention is covalently attached to hydrogel polymer matrix, by the reaction of one or more (terminal) functional groups present on the branched temperature-responsive polymer, P, of the polymer conjugate with one or more functional groups present on hydrogel polymer matrix, to form one or more of the following linking groups:

—$NR_1$—, —O—, —C(O)—O—, —O—C(O)—, —C(O)—$NR_1$—, —$NR_1$—C(O)—, —N($R_1$)C(O)O—, —O(O)CN($R_1$)—, —S—, —S(O)—, —S(O)$_2$—, —S(O)$_2$—$NR_1$, —$NR_1$—S(O)$_2$— or a triazole linking group (formed by "click" chemistry), wherein $R_1$ is hydrogen or (1-4C)alkyl (e.g. methyl).

In a particular embodiment, the polymer conjugate of the invention is covalently attached to the hydrogel polymer matrix, by the reaction of one or more (terminal) carboxyl or ester groups present on the branched temperature-responsive polymer, P, of the polymer conjugate with one or more amino groups present on the hydrogel polymer matrix, to form a —C(O)—NH— covalent attachment.

Suitably, the ester groups present on the branched temperature-responsive polymer, P, are succinimide esters groups (e.g. N-hydroxysuccinimide (NHS) or N-hydroxysulfosuccinimide (Sulfo-NHS) activated esters).

The polymer conjugate may be present in any suitable amount in the hydrogel compositions of the present invention. Suitably, the polymer conjugate is present in the hydrogel compositions of the present invention in an amount of the between 0.5 and 50 wt %. More suitably, the polymer conjugate is present in the hydrogel compositions of the present invention in an amount of the between 0.5 and 30 wt %. Even more suitably, the polymer conjugate is present in the hydrogel compositions of the present invention in an amount of the between 0.5 and 20 wt %. Most suitably, the polymer conjugate is present in the hydrogel compositions of the present invention in an amount of between 5 and 20 wt %.

In an embodiment, between 1% and 30% of the total (terminal) functional groups of the branched temperature-responsive polymer, P, are covalently attached to the hydrogel polymer matrix. Suitably, between 1% and 20% of the total (terminal) functional groups of the branched temperature-responsive polymer, P, are covalently attached to the hydrogel polymer matrix. More suitably, between 1% and 15% of the total (terminal) functional groups of the branched temperature-responsive polymer, P, are covalently attached to the hydrogel polymer matrix. Even more suitably, between 1% and 10% of the total (terminal) functional groups of the branched temperature-responsive polymer, P, are covalently attached to the hydrogel polymer matrix. Most suitably, between 1% and 5% of the total (terminal) functional groups of the branched temperature-responsive polymer, P, are covalently attached to the hydrogel polymer matrix.

It will be appreciated that the hydrogel polymer matrix may be any suitable polymer matrix that is capable of forming a hydrogel upon exposure to water. Suitable polymer matrixes are well-known in the art and may be ready selected by a person skilled in the art. Non-limiting examples of suitable hydrogel polymer matrixes include polyacrylate based polymer matrixes, polyethylene glycol based polymer matrixes, polyvinylalcohol based matrixes, polyvinylpyrrolidone based polymer matrixes, polyacrylamide based polymer matrixes and combinations thereof. Suitably, the hydrogel polymer matrix is charge neutral.

In an embodiment, the hydrogel polymer matrix is a polyacrylate based polymer matrix.

In another embodiment, the hydrogel polymer matrix is a polyacrylate based polymer matrix formed from the reaction between glycerol monomethacrylate (GMMA), glycidyl methacrylate (GME) and ethylene glycol dimethacrylate (EGDMA).

In an embodiment, the water content of the hydrogel is greater than 50% w/w and more suitably it is greater than 70% w/w.

In a further aspect, the present invention provides a contact lens, membrane, swab or wound dressing comprising a hydrogel composition as defined herein.

The present invention also provides a method of detecting the presence of fungi in a biological sample, the method comprising:
(i) contacting a polymer conjugate, composition, hydrogel composition, contact lens, membrane, swab or wound dressing as defined herein with the biological sample;
(ii) removing either the polymer conjugate, composition, hydrogel composition, contact lens, membrane, swab or wound dressing as defined herein from the biological sample and testing for the presence of bound fungi.

In yet another aspect, the present invention provides a method of determining the presence of a fungal infection, the method comprising:
(i) contacting a polymer conjugate, composition, hydrogel composition, contact lens, membrane, swab or wound dressing as defined herein with either a sample obtained from the suspected site of infection or with the suspected site of infection directly; and
(ii) removing the polymer conjugate, composition, hydrogel composition, contact lens, membrane, swab or wound dressing and determining whether any fungi are bound to the polymer conjugate, composition, hydrogel composition, contact lens, membrane, swab or wound dressing respectively.

In yet another aspect, the present invention provides a method of diagnosing the presence of a fungal infection, the method comprising:
(i) contacting a polymer conjugate, composition, hydrogel composition, contact lens, membrane, swab or wound dressing as defined herein with either a sample obtained from the suspected site of infection or with the suspected site of infection directly;
(ii) removing the conjugate, composition, hydrogel composition, contact lens, membrane, swab or wound dressing from the sample;
(iii) determining whether any fungi are attached to the conjugate, composition, hydrogel composition, contact lens, membrane, swab or wound dressing; and
(iii) optionally, determining the type of fungi detected.

The present invention also provides the use of a polymer conjugate, composition, hydrogel composition, contact lens, membrane, swab or wound dressing as defined herein for detecting the presence of fungi in a biological sample or diagnosing a fungal infection.

In order to determine whether any fungi are bound to a conjugate, composition, hydrogel composition, contact lens, membrane, swab or wound dressing of the present invention, the material can be analysed under a microscope, subject to staining techniques and then viewed under a microscope or using other techniques such as labelled ligands (e.g. antibodies) to bind to any bound fungal cell present and be detected.

In a particular embodiment, selective fluorescent staining techniques are used to identify any fungal cell present on a conjugate, composition, hydrogel composition, contact lens, membrane, swab or wound dressing of the present invention. Such techniques are known in the art.

One particular advantage of the polymer conjugates of the present invention is that they are non-toxic. Thus, any diagnostic/treatment methods used to detect and/or treat fungal infections which comprise the use of the polymer conjugates of the present invention are advantageously less toxic to human cells than similar low molar mass compounds/conjugates known in the art.

EXAMPLES

Examples of the invention will now be described, for the purpose of illustration only, with reference to the accompanying figures, in which:

FIG. 1 shows electrospray mass spectra of Amp-B: A) example of negative ion spectrum (black); B) example of positive ion spectrum (grey); Calibration curve for Amp-B using electrospray mass spectrometry.

FIG. 2 shows a) UV Spectra of Amp-B in Methanol with varying concentrations, b) GPC chromatogram UV detector response at 405 nm of Amp-B at various concentrations. c) calibration curve (at 405 nm) derived from stand alone UV/visible spectrometry and d) from GPC chromatogram (at 405 nm); (e) GPC chromatograms of Branched-PNIPAM-Amp (UV absorbance at 405 nm) and signal from refractive index detector. Also shown is the chromatogram of Amp-B alone (UV response).

Figure 5:
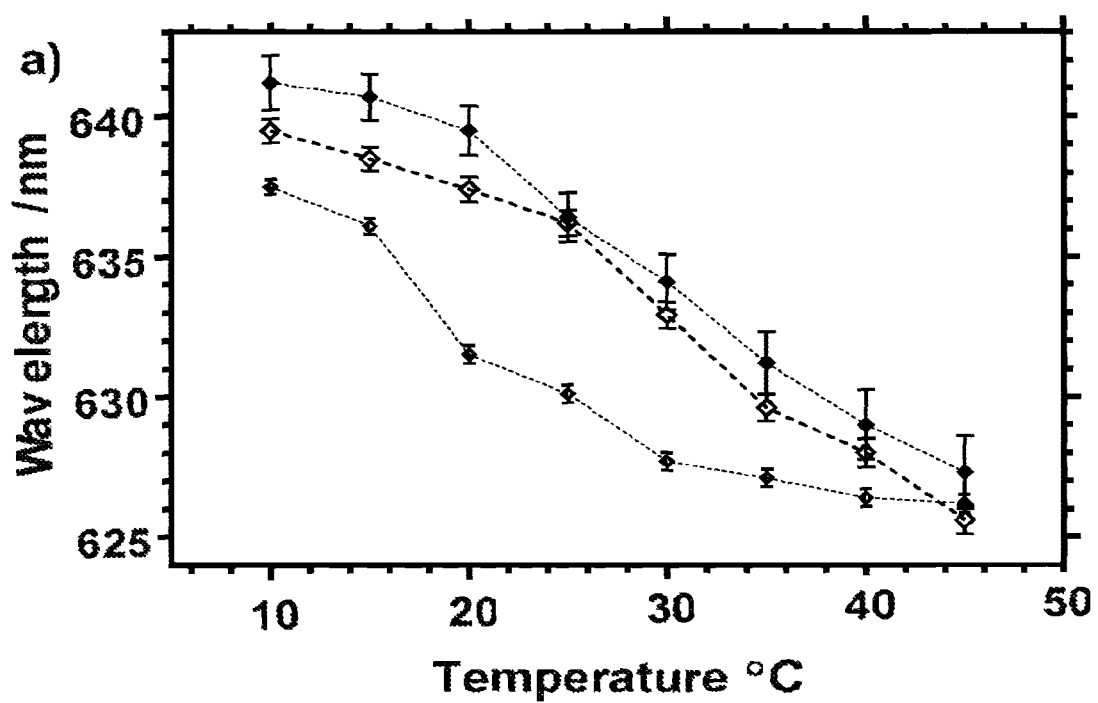
Figure 5:
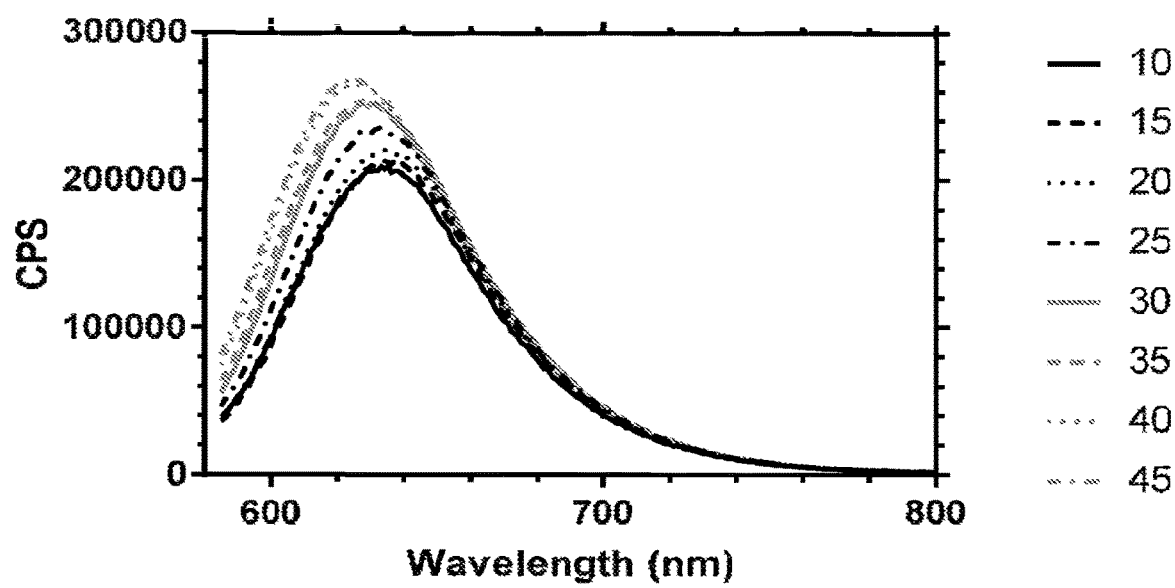
Figure 5:
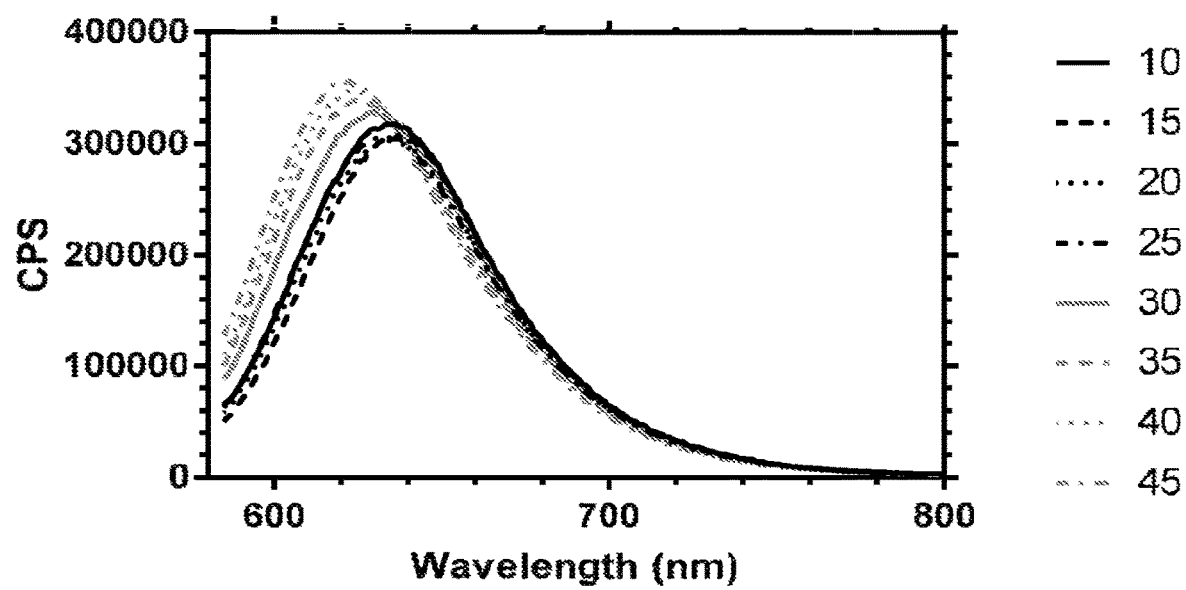

FIG. 5 shows A) the peak fluorescence emission wavelength of the spectra of nile red in solutions of Branched-PNIPAM-Amp (1 mg/ml) alone (♦); mixed with 1:1 ergosterol (◇) across $T_{CRIT}$ and the wavelength of the peak emission in the presence of Branched-PNIPAM-Py (■); B,C) Fluorescence emission spectra of nile red in solutions of Branched-PNIPAM-Amp for B) Branched-PNIPAM alone, and C) Branched-PNIPAM-Amp in the presence of ergosterol. Spectra obtained following excitation at 580 nm.

Figure 6:
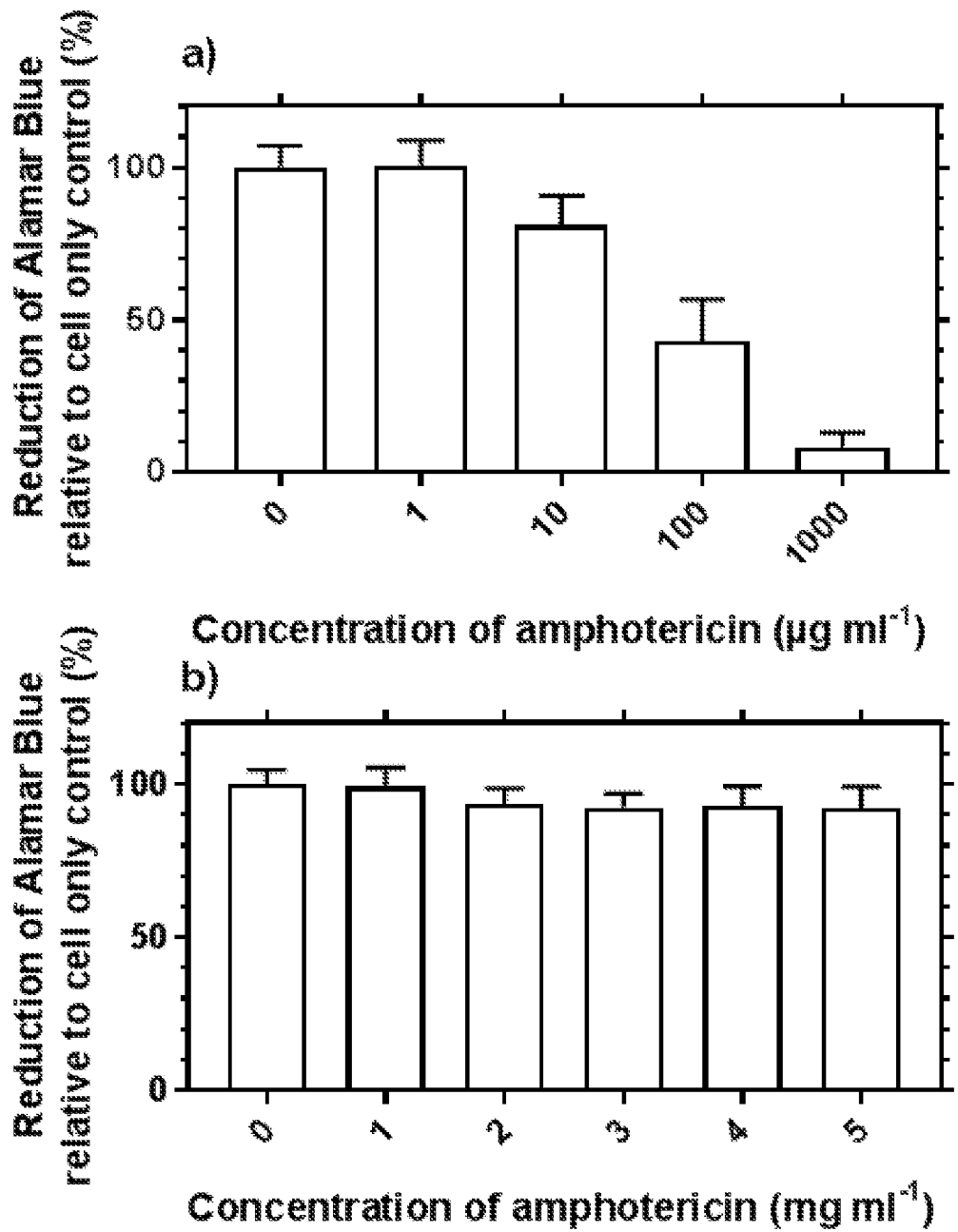

FIG. 6 Viability of rabbit corneal epithelial cells in the presence of increasing concentrations of A. Amp-B or B. branched-PNIPAM-Amp. The data show the significantly higher susceptibility of the cells to low concentrations of Amp-B and the lower toxicity of the polymer variant.

Figure 7:
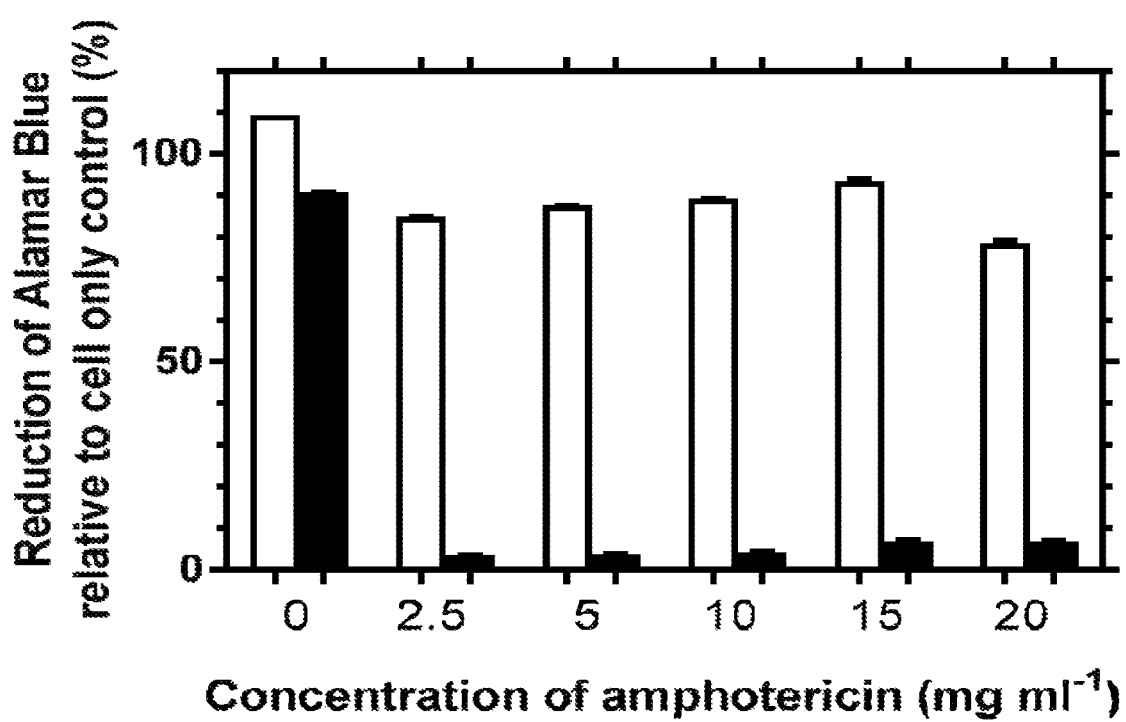

FIG. 7 shows the human corneal biocompatibility of Branched-PNIPAM-Amp (white) and free amphotericin (black).

Figure 8:
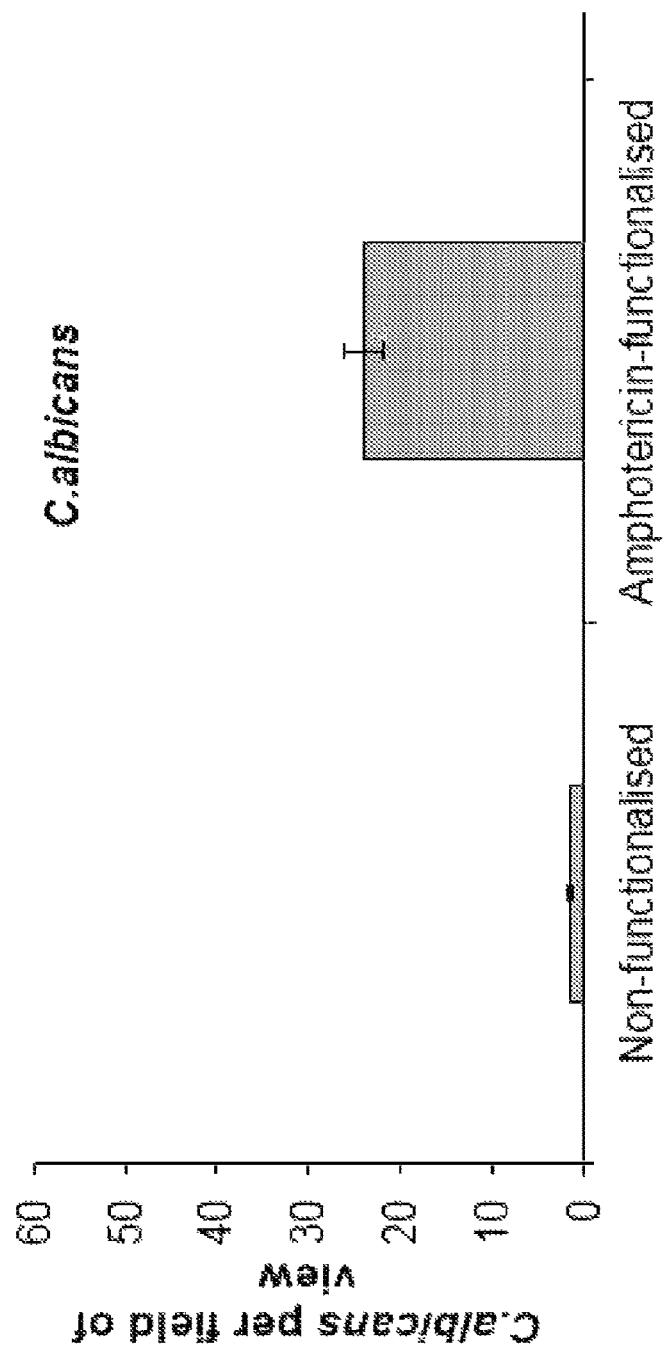

FIG. 8 shows the binding of C. albicans to functionalised hydrogels of the present invention.

Figure 9:
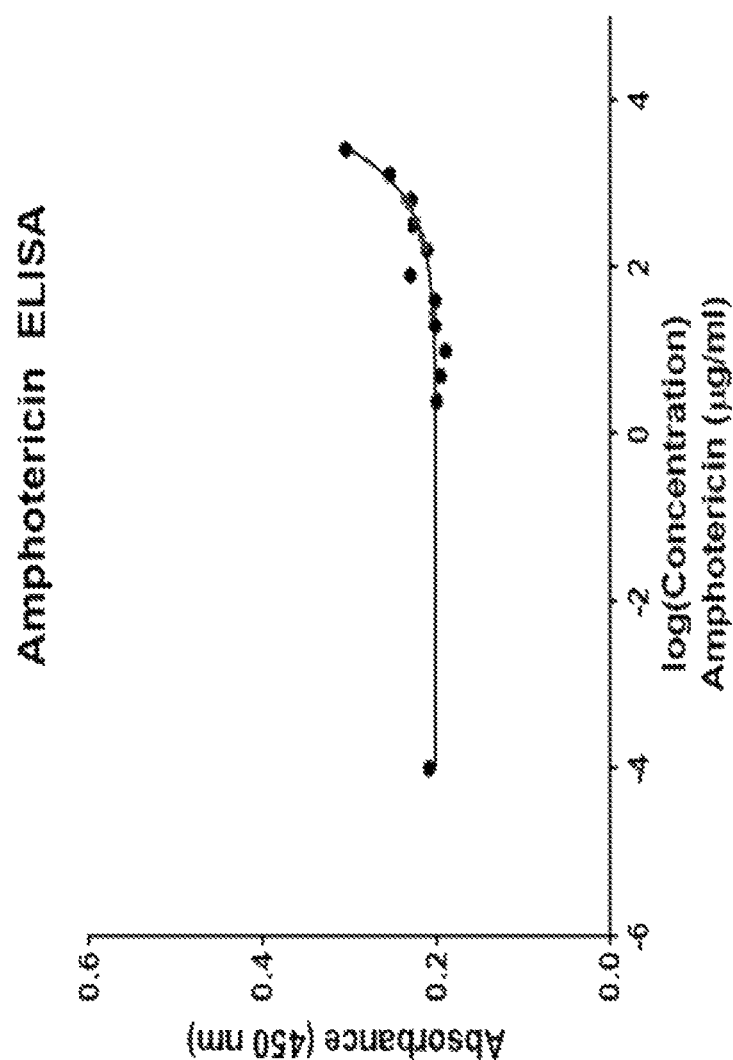

FIG. 9 shows the ELISA measurements of hydrogel discs to determine Amp-B content, where multiple samples (n=9) were analysed.

Figure 10:
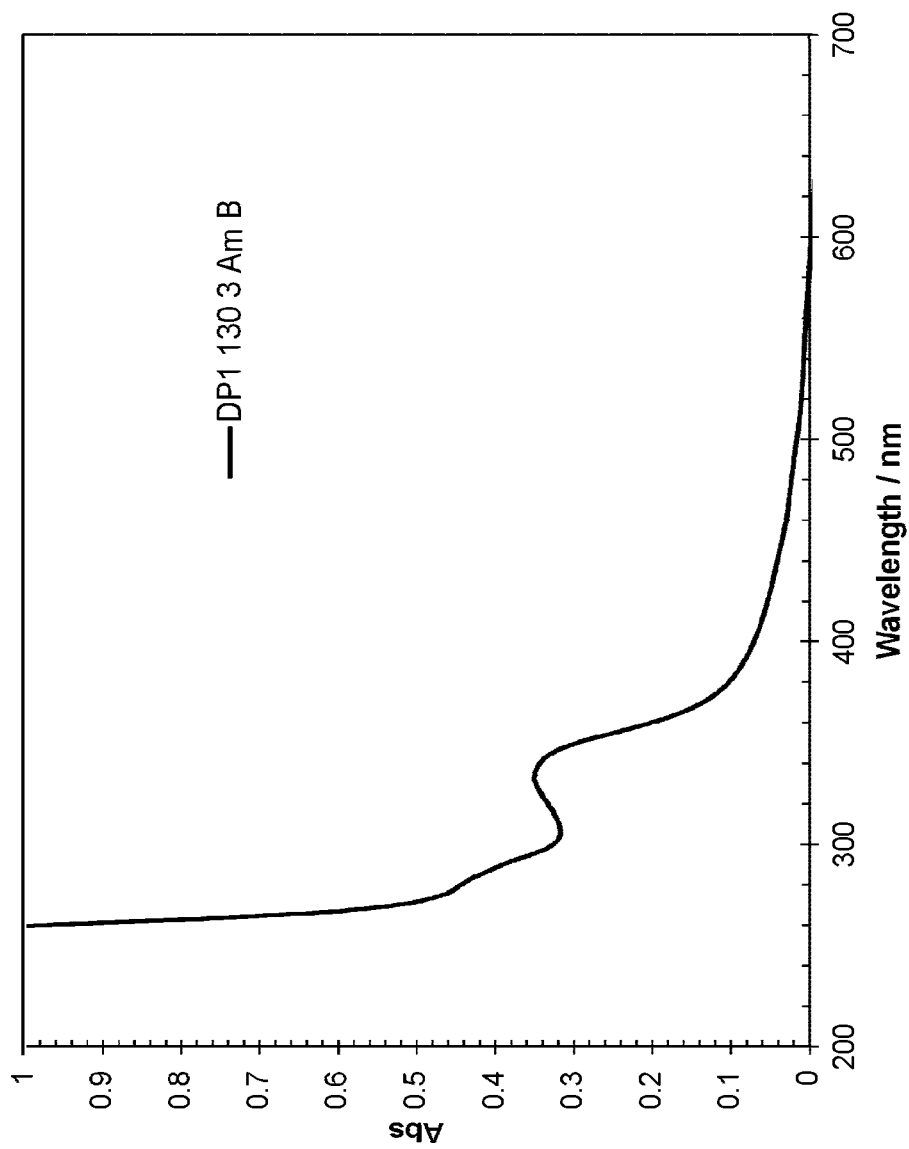

FIG. 10 shows the UV absorption data with increased AUV Absorption of amphotericin hydrogels over the base material.

Figure 11:
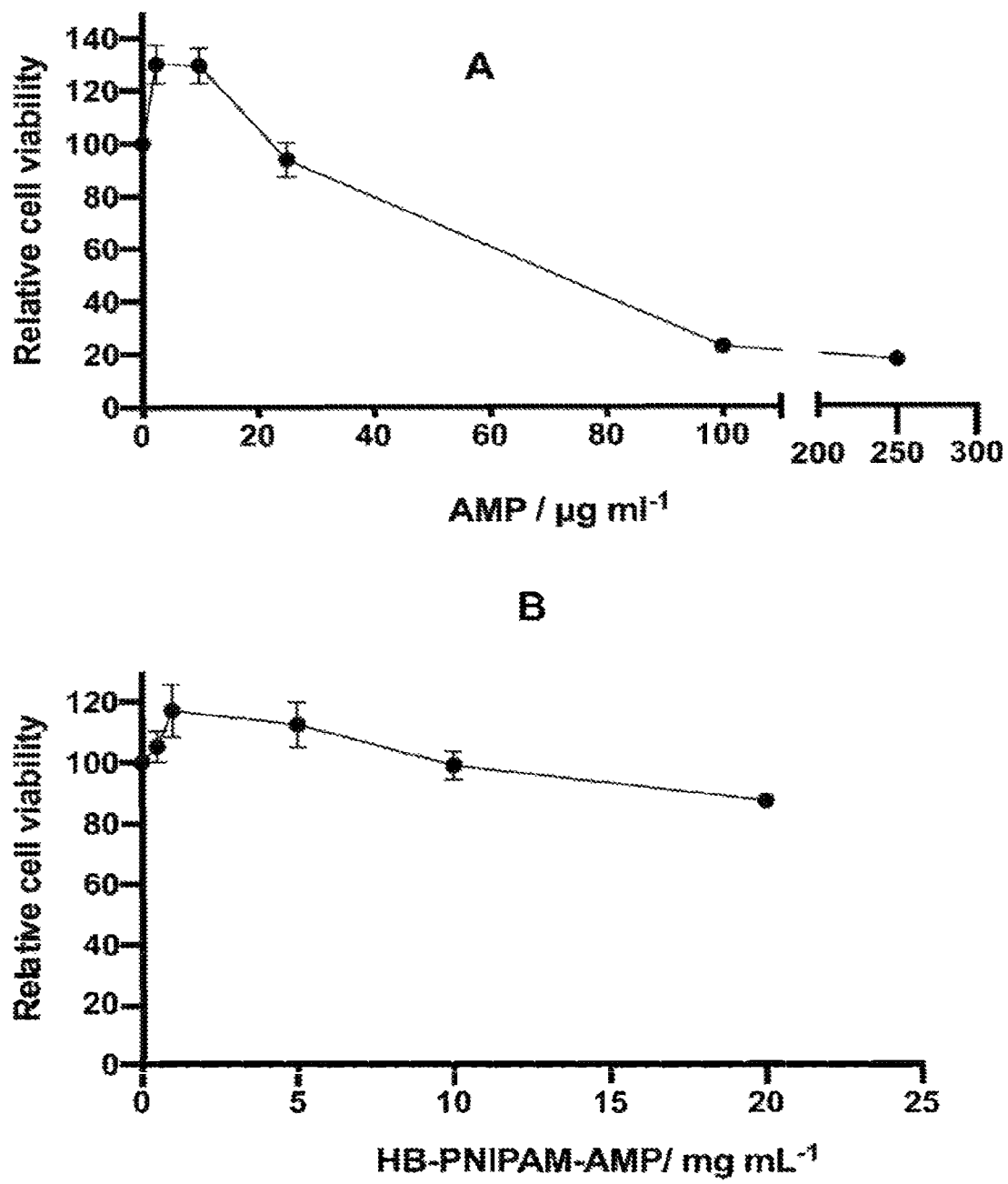

FIG. 11 shows cell viability relative to controls (in the absence of Branched-PNIPAM-Amp or Amp-B) for A) Amp-B; and B) Branched-PNIPAM-Amp, with human renal epithelial cells.

Example 1—Synthesis and Characterisation of Branched PNIPAM-Amphotericin B Conjugates (Branched-PNIPAM-Amp)

Materials and Methods

All materials were used as supplied unless otherwise stated. Stated material purities were N-isopropyl acrylamide (NIPAM) (Aldrich, 97%), N-hydroxy succinimide (Aldrich, 98%), dicyclohexyl carbodiimide (Aldrich, 98%), Amp-B (Cambridge Bioscience, >95%), dichloromethane (HPLC grade), Nile Red (Sigma, 99%) and ethyl acetate (HPLC grade) were supplied by Sigma Aldrich. N-isopropyl acrylamide was recrystallised from hexane/toluene. 4,4'-Azobis (4-cyanovaleric acid) (ACVA) (98% purity) was obtained from Alfa Aeser and dried in vacuo at room temperature overnight. Branching chain transfer agent (CTA) 4-Vinyl-benzyl-pyrrole-carbodithioate (1) was synthesised and purified according to a previously reported method.[23] Dioxane (Analar grade), diethyl ether (anhydrous), dimethyl formamide (Analar grade), ethanol (Analar grade), acetone (Analar grade) and hydrochloric acid (35% wt/wt) were obtained from VWR, Ltd. Cell culture reagents were purchased from Sigma-Aldrich unless otherwise stated. Dispase II was purchased from Roche and epidermal growth factor was purchased from Invitrogen. Mouse 3t3 fibroblasts were obtained from ATCC, Manassas, VA and an established cell line-J2 3T3 cells originally obtained from Professor Howard Green, USA. Wild brown rabbit heads were kindly provided by the BlackFace Meat Company in Dumfries, Scotland. Human corneas were obtained from Ramayamma International Eye Bank, LV Prasad Eye Institute, Hyderabad. Due to the low solubility of Amp-B[21], for biological assays, Amp-B BioReagent (Sigma-Aldrich) was used.

Synthesis of Branched-PNIPAM Precursor

Acid ended polymer was prepared via dissolution of 1 (3.667 g, 14.1 mmol), ACVA (3.96 g, 14. 1 mmol) and NIPAM (40.00 g, 353.5 mmol) in 1,4-dioxane (280 ml) to a sealed round bottom flask. This was bubbled with nitrogen for thirty minutes to degas the solvent before heating (60° C., 48 hours) under a nitrogen atmosphere. The reaction mixture was precipitated into diethyl ether and the precipitate collected and dried in vacuo overnight. The solid was weighed and characterised by $^1$H NMR [400 MHz, DMSO (ppm): 1.02 (6H, s, —N(CH$_3$)$_2$) 1.40 (2H, br m, CH$_2$—CH—Ar—) 1.95 (2H, br m, —CH$_2$—CH—CO—NH—), 3.82 (H$_2$O-polymer), 6.41 (H$_2$, br s, N-pyrrole-H), 7.13 (br m, —Ar—), 7.7 (2H br s, N-pyrrole-H)], Sulphur content (1.81%), LCST (19.0° C.) and DOSY (298 K peak $R_Hn$=2.33, $R_F$—, =2.40).

Synthesis of Branched-PNIPAM-Amp

The branched polymer above was then re-dissolved in 400 ml dimethyl formamide with additional ACVA (73.22 g, 259.2 mmol), nitrogen was bubbled through the solution which was then heated and stirred for 18 hours under nitrogen. Additional ACVA was added to the mixture (73.22 g, 259.2 mmol) which was reacted for an additional 18 hours before a final addition of ACVA (73.22 g, 259.2 mmol) and further reacted for another final 18 hours. The reaction mixture was precipitated into diethyl ether then reprecipitated from acetone into diethyl ether. The final product was dissolved in acetone with 10% ethanol and ultrafiltered three times to remove the low molar mass component, then the solvent was removed by rotary evaporation. A solid yield of 95% was characterised by $^1$H NMR ($^1$H NMR [400 MHz, DMSO (ppm): 1.02 (6H, s, —N(CH$_3$)$_2$) 1.43 (2H, br m, CH$_2$—CH—Ar—) 1.98 (2H, br m, —CH$_2$—CH—CO—NH—), 3.79 (H$_2$O-polymer), 7.17 (br m, —Ar—)], Sulphur content (0.25%), LCST (22.2° C.). The polymer was stored at −18° C. The acid ended polymer (5.00 g) was dissolved in DMF (55 ml). To this, a solution of N-Hydroxysuccinimide (0.858 g, 7.46 mmol) and N—N-Dicyclohexylcarbodiimide (DCC) (1.539 g, 7.46 mmol) in DMF (15 ml) was added. The mixture was stirred under N$_2$ overnight and all solid products removed via gravity filtration. The remaining solution was precipitated into diethyl ether, dissolved in ethanol and concentrated via ultrafiltration three times. The remaining solvent was removed by rotary-evaporation and the solid dried under vacuum at room temperature. This succinimide precursor polymer (1.00 g) was dissolved in ice-cold water (50 ml). A solution of Amp-B (30 mg, 0.032 moles) in 0.1 M sodium phosphate buffer (pH 8.5, 10 ml) and water (10 ml) was added to the polymer solution (1.0 g). Via addition of 0.01 M NaOH solution the pH was increased to pH 11 while stirring on ice overnight, then at RT for 24 hours. The solution was ultrafiltered in water using 10 kDa pore membrane filters in water at pH 11 (250 ml extracted—repeated seven times), then once again at pH 7 (250 ml extraction) before the sample was freeze-dried. The final product was a pale yellow solid (0.99 g yield) and was characterised by $^1$H NMR [400 MHz, DMSO (ppm): 1.05 (6H, s, —N(CH$_3$)$_2$) 1.55 (2H, br m, CH$_2$—CH—Ar—) 2.01 (2H, br m, —CH$_2$—CH—CO—NH—), 3.82 (H$_2$O-polymer), 7.26 (br m, —Ar—)], sulfur content (0.24%), LCST (36.0° C.) and DOSY (R$_{Hn}$=2.55 nm, R$_{Hw}$=2.66 nm) and stored at −18° C. The term "HB-PNIPAM-Amp" is used synonymously herein with "Branched-PNIPAM-Amp".

Instrumentation

Polymer characterisation was carried out by nuclear magnetic resonance (NMR) spectroscopy of solutions in DMSO-D$_6$. Measurements were obtained with a Bruker Avance spectrometer operating at 400 MHz ($^1$H) and 600 MHZ ($^{13}$C). The sulphur content was determined by elemental analysis via combustion as % of total sample by weight. LCST measurements were carried out on a Nano DSC by TA Instruments; polymer samples were dissolved in H$_2$O at 5 mg ml$^{-1}$ and stored at 5° C. for 24 hours prior to use to ensure complete dissolution. Samples were run over the temperature range 3-75° C. with a heating rate of 1.5° C. per minute and cooling rate of 1° C. per minute. The Tc-g was taken as the temperature at the thermogram peak maximum. Electrospray mass spectra were recorded using a Micromax Quattro LC from Kinesis Solutions. Amphotericin solutions were prepared in methanol (spectroscopic grade) ranging in concentration from 10 μg ml$^{-1}$ to 0.103 μg ml$^{-1}$, and additional spike solutions mixed with 0.98 mg ml$^{-1}$ NIPAM were run from 0.49-4.9 μg ml$^{-1}$ to ensure the presence of polymer did not reduce detection efficiency. Samples were injected directly into the device via a syringe pump at a rate of 10 μl min$^{-1}$. UV absorbance measurements were carried out both in-line on the GPC instrumentation (using an Agilent Infinity 1260 UV detector) and in 1 cm path length cuvettes using a Varian Cary 50 probe UV-Visible spectrometer.

Polymer molar mass distribution was recorded via gel permeation chromatography (GPC) on a methanol based system as we described previously. Samples were dissolved in methanol (1 mg ml$^{-1}$) and injected through two Agilent Polargel-M columns (high molar mass range) with a flow rate of 1 ml minute.[18] They were analysed via comparison to a universal calibration using linear PNIPAM standards via triple RI, UV and viscometric detection to give absolute molar mass averages (M$_n$, M$_w$, M$_z$ and two forms of dispersity (Đ) M$_w$/M$_n$ and M$_z$/M$_w$).

The polymer hydrodynamic radius was calculated via DOSY NMR spectroscopy to calculate diffusion (D), which was converted to hydrodynamic radius using the Stokes Einstein relationship as shown in equation 1. Sample internal viscosity (η) was found using sample solvent shift as outlined previously.[18]

$$D = \frac{k}{6\pi} \qquad \text{Eq. 1}$$

Fluorescence Dye Studies of Polymer Solutions

A stock solution of Nile red was made up by adding 2 mg of Nile red to 5 cm$^3$ DMSO. This was diluted (to 10-7 mol dm$^{-3}$) with ultrapure water. Branched-PNIPAM polymers (11 mg) were dissolved in ultrapure water (7 ml) and Nile red stock solution (100 μl) was added. The fluorescence spectrum was then recorded on a Horiba Fluoromax-4 excitation 580 nm, emission 560-800 nm, with slit widths of 1 nm. Peak wavelength emission and intensity was calculated from the Gaussian distribution of wavelengths.

Culture Conditions for *C. albicans*

*C. albicans* cells, laboratory strain SC5314 or ATCC90028, were cultured on solid BHI (Oxoid) medium at 37° C. for 24 hours and stored at 4° C. for up to one month. Prior to experiments, a colony of *C. albicans* was sub-cultured into liquid BHI medium overnight at 37° C.

Isolation and Culture of Rabbit Limbal Epithelial Cells

Limbal rims from corneal-scleral buttons were excised from wild brown rabbit heads, as previously described.[22] Tissue was immersed in 2.5 mg ml$^{-1}$ (w/v) dispase II solution in DMEM for 1 hour at 37° C. The limbal rims were subsequently scraped gently using forceps to remove the epithelial cells. The dispase-cell suspension was centrifuged at 200 g for 5 minutes and re-suspended in culture medium containing DMEM: Ham's F12 (1:1) supplemented with 10% foetal calf serum, 100 U ml$^{-1}$ penicillin and 100 U ml$^{-1}$ streptomycin, 2.5 μg ml$^{-1}$ Amp-B, 5 μg ml$^{-1}$ insulin and 10 ng ml$^{-1}$ epidermal growth factor. Cells were cultured with irradiated 3T3-mouse fibroblasts at a cell density of 2.4×10$^4$ cells cm$^{-2}$ in culture medium. Cells were not used beyond passage 3. For experiments, cells were seeded into 24 well-plates at 5×10$^4$ cells per well and cultured for 24 hours.

Rabbit Limbal Epithelial Cell Viability

Prior to determining the viability of rabbit limbal epithelial cells, cells were washed 3× with phosphate-buffered saline (PBS, 0.01M, pH 7.4) to remove residual antimicrobials. Branched-PNIPAM-Amp (20, 15, 10, 5, 4, 3, 2, 2.5, 1 and 0 mg ml$^{-1}$) or Amp-B (0, 1, 10, 100, 1000 μg ml$^{-1}$ or 0, 2.5, 5, 10, 15, 20 mg ml$^{-1}$) were dissolved in culture medium without penicillin, streptomycin or Amp-B, and added to pre-seeded epithelial cells or human donor corneas (halved) for a further 24 hours. Epithelial cell/cornea viability was determined using Alamar Blue reagent (5 μg ml$^{-1}$) dissolved in PBS. Cells/corneas were incubated with Alamar Blue for 30 minutes and the fluorescence of the solution determined at 570 nm excitation and 585 nm emission (Infinite 200, Tecan). Data for each polymer is presented as percentage viability relative to an untreated control. Each assay was performed in triplicate and data represents the mean±SD from three independent experiments. The decrease in cellular viability after exposure to Branched-PNIPAM-Amp or Amp-B compared with a cell only control was determined using a Student's t test for single comparisons or ANOVA for multiple comparisons.

Human Renal Epithelial Cell Viability

HREpCs were cultured in renal epithelial cell growth medium 2 (PromoCell, ready-to-use) supplemented with fetal calf serum (0.05 ml ml$^{-1}$) and Epidermal growth factor (10 ng ml$^{-1}$) Insulin (5 ug ml$^{-1}$), Epinephrine (0.5 ug ml$^{-1}$), Hydrocortisone (36 ng ml$^{-1}$), Transferrin, holo (5 ug ml$^{-1}$) and Triiodo-L-thyronine (4 μg ml$^{-1}$). 10 ml of complete medium was placed into T75 flask in the incubator in a humidified atmosphere of 5% CO$_2$, at 37° C. for 30 minutes. Cryopreserved HREpCs were placed in a 37° C. water bath for 90 s with constant agitation. The cells were pipetted up and down and then quickly transferred to the pre-warmed flask. The cells were incubated for a minimum of 16 hours before changing the medium. Subsequent media changes were performed every 2-3 days until the cells were confluent.

Cells were seeded with various concentrations of the polymers and the cell viability was determined with a MTT assay relative to a control with no polymer.

Minimal Inhibitory Concentrations (MICs) for Amphotericin Polymers

*C. albicans* cells, laboratory strain SC5314 or ATCC90028, were cultured on solid BHI (Oxoid) medium at 37° C. for 24 hours and stored at 4° C. for up to one month.

Prior to experiments, a colony of C. albicans was sub-cultured into liquid BHI medium overnight at 37° C. Overnight cultures of C. albicans were adjusted to an optical density at 600 nm of 0.1 and incubated with Amphotericin polymers, which were serially diluted 1:2 from 2500-2.44 µg/ml, for 16 hours in a 96 well plate. The concentration of polymer at which there was no visible growth was determined to be the MIC. C. albicans (Robin) ATCC200955, C. tropicalis ATCC200956, A. flavus ATCC16883 and F. keratoplasticum ATCC36031 were similarly cultured on solid Sabrauds (Oxoid) medium at 37° C. for 24 hours and stored at 4° C. for up to one month. Prior to experiments, colonies were sub-cultured into liquid Sabrauds medium overnight at 37° C. All liquid cultures were static apart from A. flavus which was incubated shaking at 100 rpm.

Solubility of Branched-PNIPAM-Amp

Solutions of up to 300 mg ml$^{-1}$ of Branched-PNIPAM-Amp were found to be stable for 24 hours on a workbench. In the same timeframe solutions of 400 mg ml$^{-1}$ fully dissolved but became a viscous gel.

Analysis of Amphotericin

Figure 1:
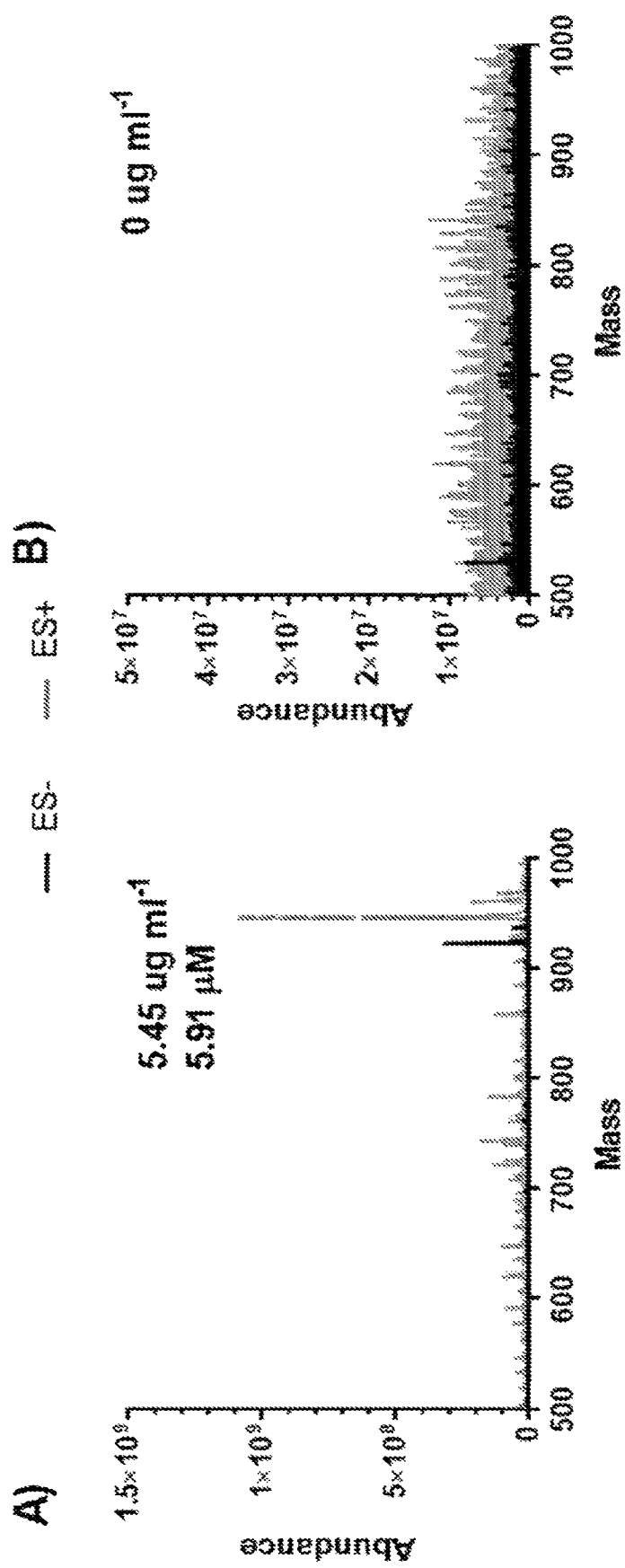
Figure 1:
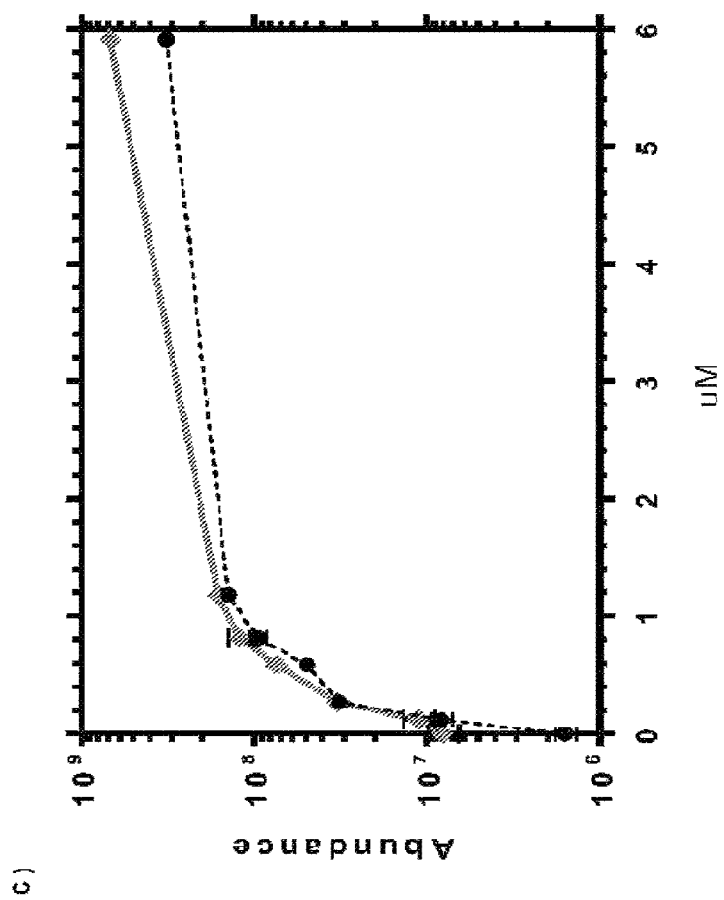
Figure 2:
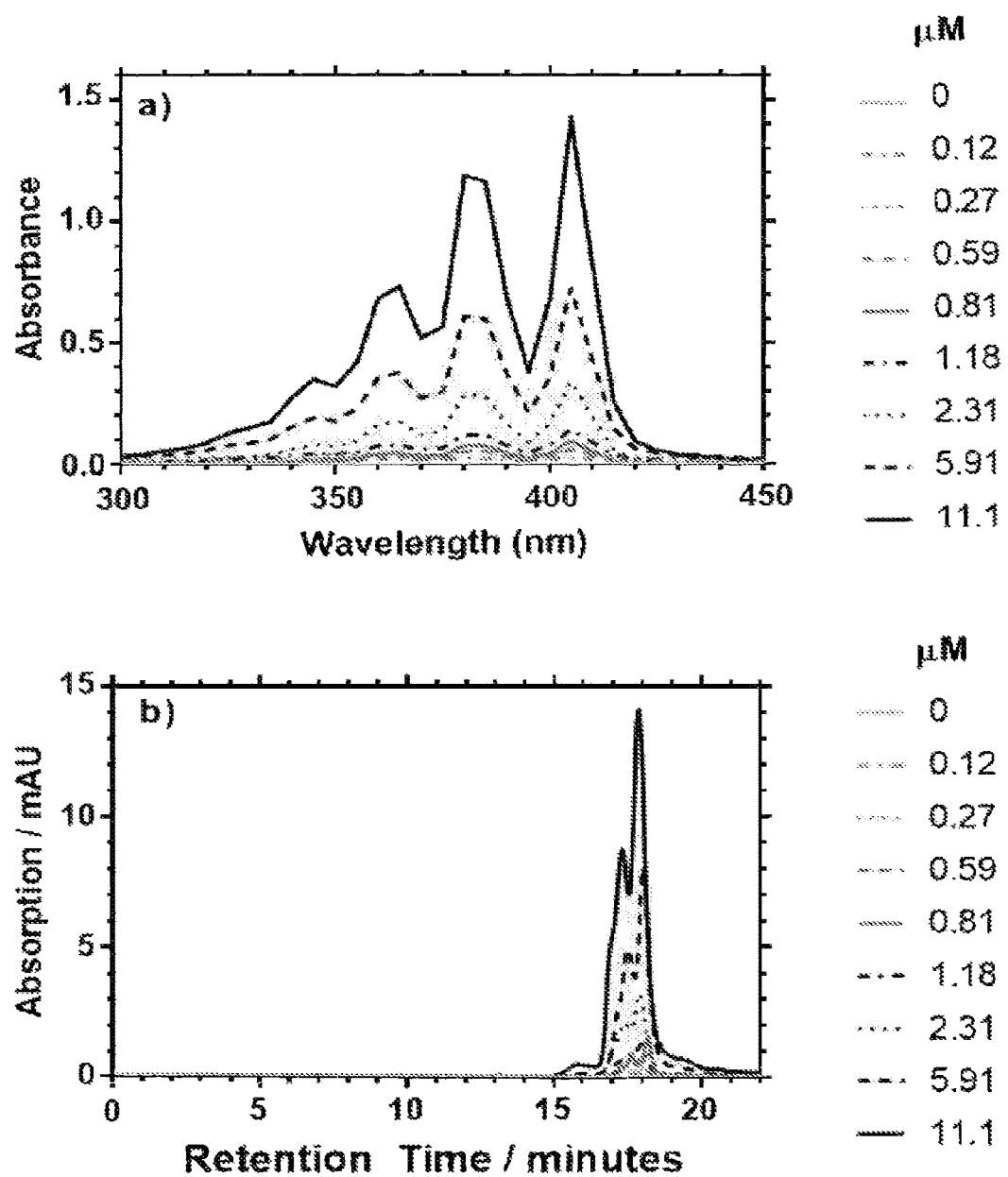
Figure 2:
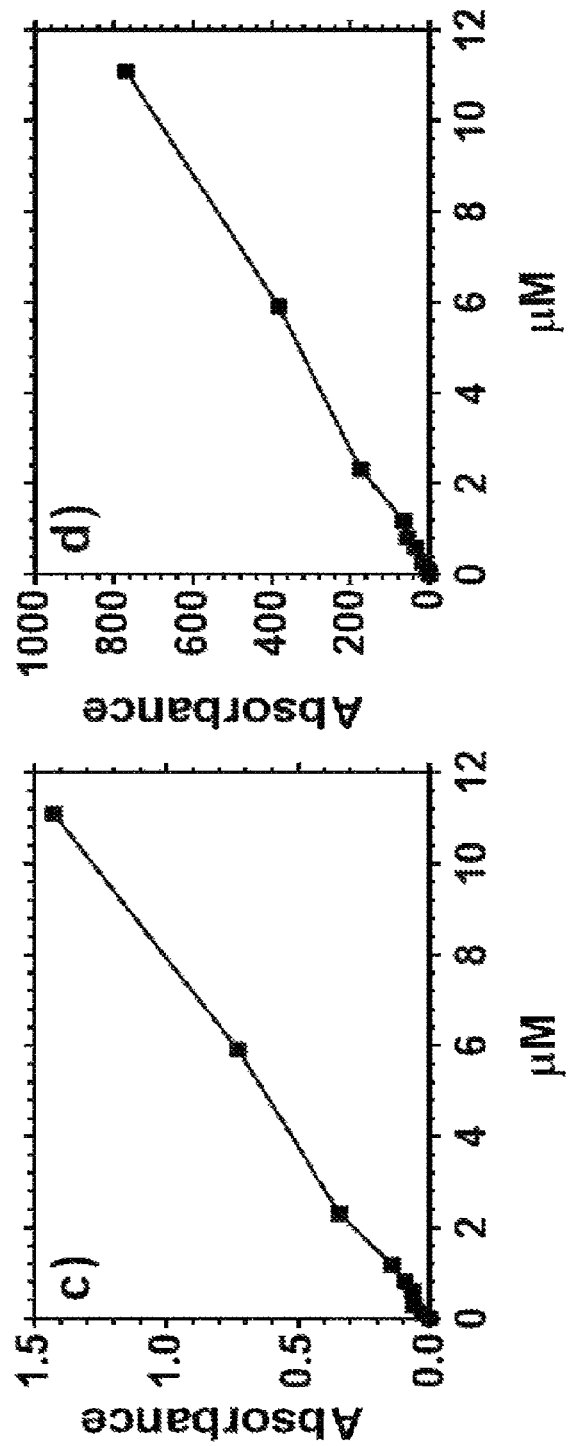
Figure 2:
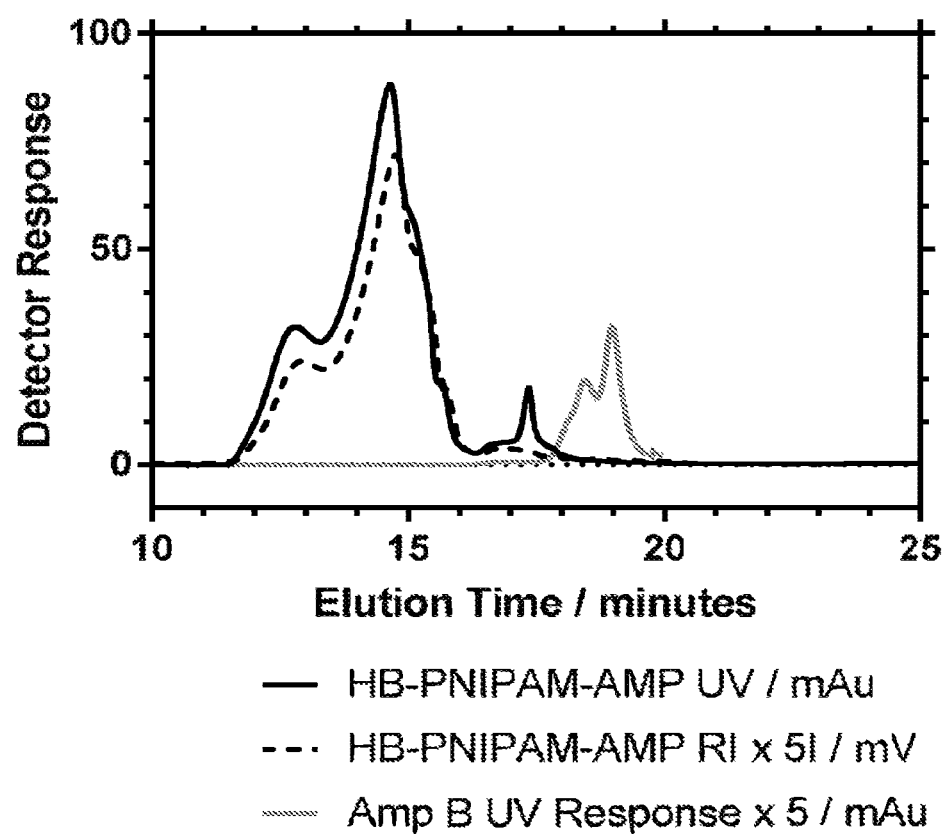

The purity of Amp-B used in the synthesis and for calibration of UV absorbance detectors was confirmed using HPLC-MS following previous published protocols.[15] The material was a mixture (geometric isomers) of polyenes of similar mass with m/z 922 (see supporting information). The MIC for Amp-B is 0.625-4 mg/L[16] (with strains with MIC<1 mg/L being regarded as resistant by Cordeiro et al) and so a method of detection for free drug needed to be established which was sensitive below this concentration to ensure no residual unattached active agent remained post polymer functionalisation. This was carried out via two methods; firstly direct injection via mass spectroscopy (FIG. 1) and gel permeation chromatography (GPC) with detection by UV absorbance (FIG. 2).

Calibration measurements of low concentration Amp-B in methanol were undertaken to determine the lower limit of detection of the drug via direct injection electrospray mass spectrometry. FIG. 1 presents the data via both ES+ and ES− and clear peaks from the drug were observed at 922 and 947 m/z respectively. Greater fragmentation was observed in the ES+ mode giving significant peaks at 648 and 620 alongside greater residual noise. It was found that the mass spectrometer was sensitive to concentrations down to 0.27 µM, far below the target concentration. When the determination was used to examine the concentration of free Amp B in the polymer sample no Amp-B could be detected. This test was repeated in the presence of non-functionalised polymers and only a slight reduction in sensitivity was observed.

Due to its high extinction coefficient an alternative measurement of Amp-B was made using UV absorbance. The molar absorption coefficient was found to be the same via whole-solution absorbance and via the in-line GPC detector (9×10$^{11}$ mol$^{-1}$ cm$^{-1}$) (FIG. 2). For both methods, the same limit of detection (0.27 µM) was observed. FIG. 2 compares the chromatogram of an Amp-B functional polymer to free Amp-B. The retention time for Amp-B is clearly seen but this peak is absent in the polymer sample.

In Vitro Interaction of Microorganisms with Polymer-Linked Hydrogels

10$^3$ FITC labelled S. aureus, P. aeruginosa or C. albicans were incubated in vitro with amphotericin-functionalised hydrogels for 1 hour. Hydrogels were washed 3 times with PBS, then imaged using a fluorescence microscope (Axiovert 200M, Zeiss) and the imaging software AxioVision Rel. 4.8 in UK and ProgRes CapturePro 2.5 software (Jenoptik) in India.

Results and Discussion

Polymer Synthesis and Characterisation

Branched poly(N-isoproylacrylamide) with a high concentration carboxylic acid end groups was synthesised via the method reported previously[17] using self-condensing vinyl reversible addition-fragmentation transfer polymerisation (SCVP-RAFT) in the presence of a vinyl functional benzyl dithioate ester (4-vinylbenzyl-pyrrolecarbodithioate, VPC) which acted as a branching agent, producing polymer with pyrrole end groups (Branched-PNIPAM-Py). The ratio of NIPAM:VPC in the monomer feed was 25:1 The final conversion of monomer was 95%. The chain ends were then modified to carboxylic acid and amidated with amphotericin B (Amp-B) via activation of the end groups as the succinimidyl ester. The reaction was carried out at pH 11 to fully solubilise the Amp-B. The Branched-PNIPAM-Amp was purified by repeated precipitation into diethyl ether, and then ultrafiltration in water through a 10 kDa membrane filter to retain only high molar mass material. The feed, molar mass averages and functionality are set out in Table 1.

TABLE 1

Synthesis of Branched-PNIPAM-Amp polymers; Feeds in the functionalisation reactions, molar masses and functionalities.

| Branched-PNIPAM/g | Amp-B/g | $M_n^a$ | $M_w^a$ | $M_z^a$ | $F^b$ |
|---|---|---|---|---|---|
| 1.00 | 0.03 | 8,534,100 | 8,990,250 | 1.05 | 18.3% |

Figure 3:
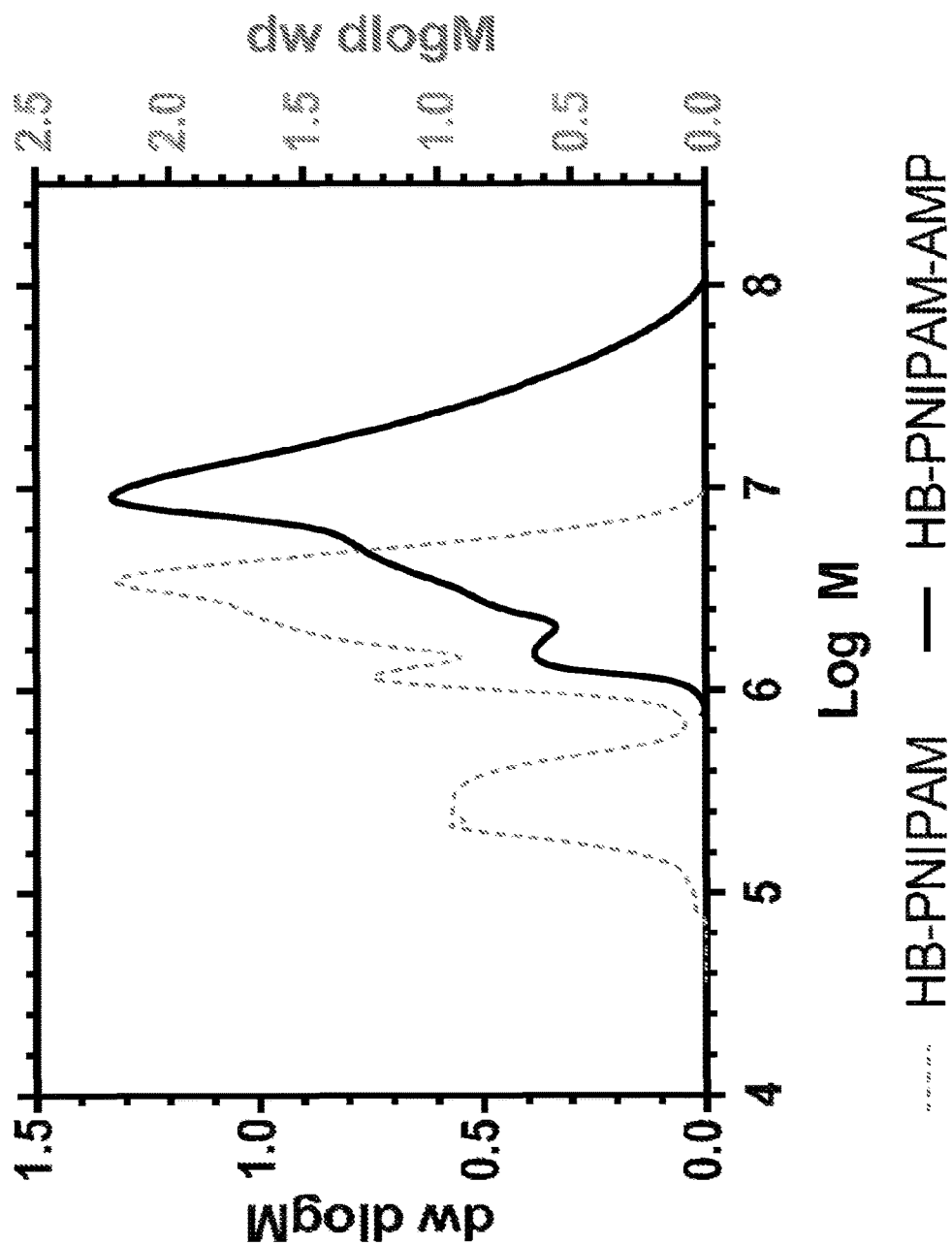
FIG. 3 shows the Molar Mass Distribution of Branched-PNIPAM-Amp.

$^a$Molar masses (kg mol) were obtained by gel permeation chromatography in methanol.
$^b$Functionality (F) expressed as molar percentage of chain ends carrying an Amp-B moiety Additional reactions were carried out with increased feeds of Amp-B. However, feeds in excess of that shown provided polymer material contaminated with free Amp-B and this was difficult to remove. Branched-PNIPAM-Amp produced by this procedure and after multiple precipitations and ultra-filtration cycles is a high molar mass material with broad polydispersity. This is illustrated by the molar mass distribution, derived from gel permeation chromatography (GPC), of Branched-PNIPAM-Amp, which is shown in FIG. 3.

Figure 4:
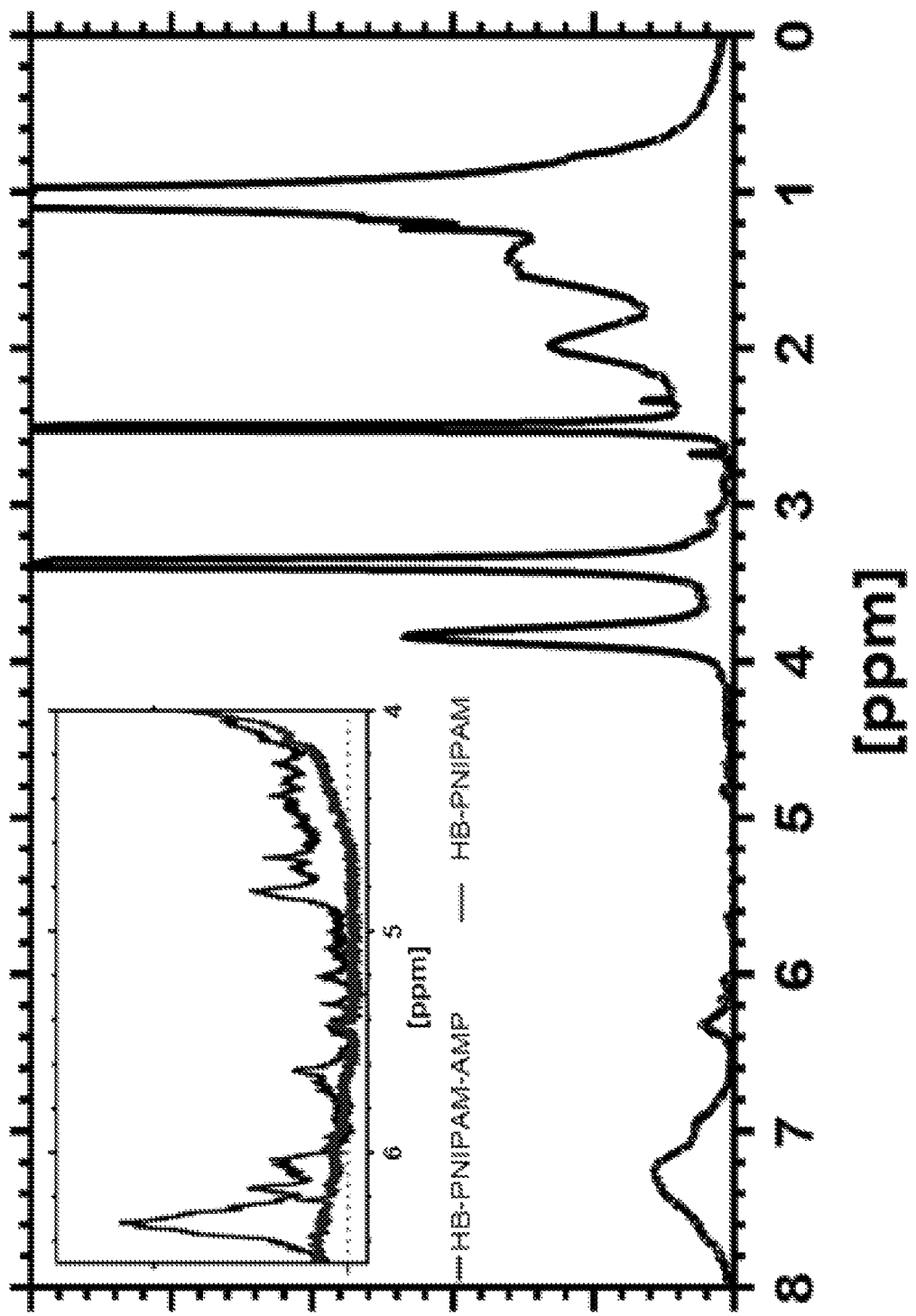
FIG. 4 shows the $^1$H NMR analysis of Branched-PNIPAM-AMP polymer with focus on 4-6 ppm (inset). Non-functionalised Branched-PNIPAM provided for reference.

The presence of amphotericin on polymer chains was demonstrated by $^1$H NMR spectroscopy as shown in FIG. 4. The functionalisation with Amp-B and is demonstrated by the peaks arising between 4 and 6.5 ppm from the newly incorporated polyene ring.

DOSY NMR was also used to reveal the polymer hydrodynamic radii ($R_H$) distribution in DMSO[18] the spectrum is provided in the supporting information. This technique showed that $R_{H,n}$=2.55 nm and $R_{H,w}$=2.60 nm. The spectra also showed that within the limits of detection of the nmr technique the Branched-PNIPAM-Amp contained negligible amounts of Amp-B that was not attached to the polymer end groups. Mass spectrometry and UV absorbance at 405 nm was used to further examine the presence of residual Amp-B.

Mass Spectrometry of Branched-PNIPAM-AMP was carried out on a Micromas Quattro LC from Kinesis Solutions via direct injection of polymer into the detector (10 µg ml$^{-1}$) in spectroscopic grade methanol. It was determined that there was no free Amp-B within the polymer by the absence of peaks m/z 922 corresponding to Amp-B.

FIG. 1 shows: A) the mass spectrometry data of Amp-B in MeOH following direct injection (ES− black, ES+ grey) with varying concentrations; and B) border inserts average abundance response of detector to Amp-B injection (n=3).

UV absorbance measurements were carried out on Branched-PNIPAM-AMP samples and the concentration of Amp-B determined via the Beer Lambert equation. FIG. 2 provides the in-line UV absorbance detector demonstrated that Amp-B was equally distributed across the polymer molar mass distribution. This indicated that the polymer contained amphotericin functionality irrespective of the molar mass of the polymer. Also, no separate peaks were observed due to free Amp-B. Additional experiments were carried out using a Varian Cary 50 spectrometer and the total absorbance of the solution examined. The sum UV absorbance of the in-line detector and the solution gave equivalent molar absorption coefficients with respect to concentration.

The data confirms that Amp-B was successfully attached to the polymer chain ends via the succinimide reaction and that there were negligible amounts of residual Amp-B following the purification process.

Polymer Solution Properties

The solution properties of branched poly(N-isopropylacrylamides) are highly dependent on chain end effects as we have previously described.[19] The polymers are responsive to temperature and show a lower critical solution temperature (LCST) ($T_{crit}$). The $T_{crit}$ of these polymers (determined by calorimetry) are shown in Table 2 below. The data show that functionalisation with Amp-B led to an increase in $T_{crit}$.

TABLE 2

$T_{crit}$ of Branched-PNIPAM

| Polymer | $T_{crit}$ [a] |
| --- | --- |
| Branched-PNIPAM-Py | 19.0 |
| Branched-PNIPAM-COOH | 22.2 |
| Branched-PNIPAM-Amp | 36.0 |

[a] Determined by microcalorimetry (1 mg ml$^{-1}$)

The $T_{crit}$ occurs at a coil-to-globule transition involving segmental desolvation and this can be monitored using the addition of solvatochromic fluorescence dyes such as nile red[15, 21]. The emission wavelength of the nile red dye reflects the average internal polarity of the chain segments between the swollen and desolvated forms. Decreasing peak wavelength of the emission spectra indicates increasing hydrophobicity of the environment as it partitions into more hydrophobic (desolvated) domains. Nile red is thus a useful probe that can used to examine changes in the solvation of chain segments on binding of the end groups.

A solution of Branched-PNIPAM-Amp was mixed with nile Red and studied both in the presence and absence of Ergosterol across a temperature range 5-45° C. (FIG. 5). The data shown in FIG. 5 showed a decrease in wavelength of nile red in with temperature in both the presence and absence of ergosterol when the dye was mixed with Branched-PNIPAM-Amp. However, at all temperatures the spectra shifted to lower wavelength on addition of ergosterol. Also, comparison of data obtained from Branched-PNIPAM-Amp to that obtained from Branched-PNIPAM-Py showed that the polymer with pyrrole end groups provided a much more desolvated environment at all temperatures and the data indicated that the $T_{crit}$ occurred at around 19° C. in this polymer compared to the broad decrease in wavelength (24 to 40° C.) observed with Branched-PNIPAM-Amp. The data are thus in agreement with the increase in $T_{crit}$ following modification to the provide the Amp-B end groups observed by calorimetry.

Therefore, these data indicate that on addition of ergosterol it binds to the Amp-B ligands at the chain ends of Branched-PNIPAM-Amp and this binding induces a segmental desolvation that reduces the average polarity of the environment in into which nile red is portioned. The results show an interaction between the highly-branched polymer chain ends and the target ergosterol which will be located at the surfaces of fungi.

MICs for Branched-PNIPAM-Amp

Amp-B and Branched-PNIPAM-Amp were incubated with *C. albicans* to determine the minimal inhibitory concentration (MIC) (Table 3a). Only polymers containing the Amp-B drug were found to be effective against the fungi. The MIC of Amp-B was different for two different strains of *C. albicans*. However, there was little difference between the efficacy of the polymer to the two different strains. Importantly, the weight-based calculation of the MIC for the ATCC90028 strain was the same regardless of whether Amp-B or Branched-PNIPAM-Amp was used. The molar density of Amp B is 1.19 mmol g$^{-1}$ (M=838 g mol$^{-1}$) and that of Branched-PNIPAM-Amp is 0.25 mmol g$^{-1}$. Therefore, on a molar basis the Amp-B is more effective against *C. albicans* strain ATCC90028 and the molar MIC against is approximately double that of Amp-B against strain SC5314. These figures indicate that Branched-PNIPAM-Amp could be an effective therapeutic agent against *C. albicans*. However, it is well known that Amp B is insoluble in water and saline solution at physiological pH. Conversely up to 300 mg ml$^{-1}$ of Branched-PNIPAM-Amp polymer can be dissolved before viscous gelation starts to occur. The increase in solubility of Branched-PNIPAM-Amp compared with Amp-B is a significant advantage for medical applications. Amp-B is also known to be highly toxic and is thus only used as "last resort" anti-fungal. Therefore, the two compounds were compared for their toxicity against rabbit limbal epithelial cells and human donor corneas to determine whether Branched-PNIPAM-Amp could be a viable and less cytotoxic alternative to the use of Amp-B.

Table 3b shows MIC values for Amp-B, Branched-PNIPAM-Py and Branched-PNIPAM-Amp for two Amp-B sensitive (SC5314, ATCC90028). and non-sensitive (ATCC200956, ATCC 200955) *Candida* strains, as well as for *Aspergillus flavus* ATCC16883 and *Fusarium* keratoplasticum ATCC36031, both Amp-B sensitive.

TABLE 3a

MIC values for Branched-PNIPAM-Amp and Amp-B for two *C. Albicans* strains

| Sample | MIC against SC5314 μg ml$^{-1}$ | MIC against ATCC90028 μg ml$^{-1}$ |
| --- | --- | --- |
| Amphotericin B | 0.4 | 4 |
| Branched-PNIPAM-Py | >2500 | >2500 |
| Branched-PNIPAM-Amp | 4.9 | 4 |

TABLE 3b

MIC values for Amp-B, Branched-PNIPAM-Py and Branched-PNIPAM-Amp for various Candida strains, as well as for *Aspergillus flavus* ATCC16883 and *Fusarium keratoplasticum* ATCC36031

| | Weight based MIC*/ µg mL | | | Molar MIC/ µmol mL$^{-1}$ | | |
|---|---|---|---|---|---|---|
| | Amp-B | Branched-PNIPAM-Py | Branched-PNIPAM-Amp | Amp-B | Branched-PNIPAM-Py | Branched-PNIPAM-Amp |
| *C. albicans* SC5314 | 0.4 | >2500 | 4.9 | 0.5 | — | 1.2 |
| *C. albicans* ATCC90028 | 0.5 | >2500 | 4 | 4.8 | — | 1.0 |
| *C. albicans* ATCC200955 | >2500 | >2500 | >2500 | — | — | — |
| *C. tropicalis* ATCC200956 | >2500 | >2500 | >2500 | — | — | — |
| *A. flavus* ATCC 16883 | 1.5 | >2500 | 500 | 1.8 | — | 125 |
| *F. keratoplasticum* ATCC 36031 | 0.2 | >2500 | 6.25 | 0.25 | — | 1.6 |

*Molar densities Amp-B = 1.19 × 10$^{-3}$ µmol µg$^{-1}$; Branched-PNIPAM-Amp = 0.25 × 10$^{-3}$ µmol µg$^{-1}$

Cytotoxicity

The metabolic activity of rabbit limbal epithelial cells in the presence of Amp-B and Branched-PNIPAM-Amp was determined. By assessing the reduction of Alamar Blue substrate, as the concentration of Amp-B increased there was a dose-dependent decrease in the metabolic activity of the cells, as shown in FIG. 6. There was a significant reduction ($p<0.01$) in the metabolic activity of cells after exposure to 100 µg ml$^{-1}$ Amp-B compared with the cell only control (42.8±13.9% and 100±7.1%, respectively), suggesting that a concentration of 100 µg ml$^{-1}$ would damage approximately half of cells in the area in which it was applied. For ophthalmic use, the main topical concentration of Amp-B used is approximately 1.5 mg ml$^{-1}$.[20] At a concentration of 1 mg ml$^{-1}$ there was significant decrease ($p<0.01$) in epithelial cell viability of approximately 91.7% relative to a cell only control. Importantly, this level of loss in cell viability was not observed for Branched-PNIPAM-Amp, even at 5 mg ml$^{-1}$. This concentration is in excess of what is required for inhibiting the growth of *C. albicans*. Data suggests that weight for weight, amphotericin polymer is less 'toxic' to limbal epithelial cells than Amp-B.

The examination of the cytotoxicity was further examined on ex vivo human corneas. FIG. 7 shows that cellular toxicity was not observed for Branched-PNIPAM-Amp, where there was a large decrease for Amp-B. As Amp-B is topically applied to the cornea in instances of fungal keratitis, human donor corneas were exposed to Branched-PNIPAM-Amp (0, 2.5, 5, 10, 15, 20 mg ml$^{-1}$ in DMEM), for 48 hours and the biocompatibility determined using Alamar Blue. Only a loss of 20% viability was observed, even at very high concentrations of Branched-PNIPAM-Amp, e.g. 20 mg ml$^{-1}$. However, at concentrations of only 2.5 mg ml$^{-1}$ of Amp-B there was a significant loss of corneal viability ($p<0.01$), by approximately 95%. This indicated 2.5 mg ml$^{-1}$ amphotericin can damage a cornea, whereas Branched-PNIPAM-Amp allows a high dose treatment without corneal damage at concentrations greater than the MIC for fungi.

The assessment of cytotoxicity was further examined on human renal epithelial cells. The results are illustrated in FIG. 11.

Construction of Functional Hydrogels

Glycerol monomethacrylate (GMMA) (5 g, 4.660 ml), glycidyl methacrylate (gme) (0.345 g, 0.321 ml) and ethylene glycol dimethacrylate (EGDMA) (0.206 g, 0.196 ml) were degassed via bubbling dry nitrogen through solution whilst stirring in isopropanol (2 ml) for twenty minutes. 2-hydroxy-2-methylpropiphenone (HMPP) (55 mg) was added and the solution degassed for a further five minutes before it was extracted using a glass syringe and directly injected into a quartz plate mould separated with a 0.5 mm PTFE gasket. The two quartz plates were laminated with poly(ethylene teraphthalate) sheet, which was adhered to inner surfaces of the glass, to aid the release of the produced polymer sheet. To initiate polymerisation the mould was irradiated by a 400 w metal halide UV-A lamp for 3 minutes before being turned over and irradiated on the alternate side for a further 3 minutes. The cured hydrogel sheet was then removed and immersed in isopropanol. The hydrogel sheet was washed a total of five times with fresh isopropanol and left for at least 1 hour each time before being added to a 1,3-diaminopropane in isopropanol (20% v/v, 250 ml) solution for 48 hours, being inverted half way through. It was then washed and immersed for 1 hour in isopropanol a further two times. The hydrogel was characterised by measurement of equilibrium water content (EWC=61%, SD=4%, n=12). Fourier Transform Infrared spectroscopy (FTIR) was used to analyse for residual monomer leaching and the material was imaged using scanning electron microscopy and shown to provide a flat, uniform, crack free surface.

Hydrogel with Functionalised Polymer (Branched-PNIPAM-Amp)

Aminated hydrogels were exposed to Branched-PNIPAM-Amp (50 mg) and dissolved in isopropanol (100 ml). The hydrogel sheets (90×90×0.5 mm) were immersed for 48 hours on a low speed shaker with inversion after 24 hours. Following the reaction, it was washed twice with pure isopropanol and left for one hour each time. Polymer films were characterised by assessing equilibrium water content (EWC) (see Table 4) and FTIR. Drug loading on these sheets was determined by both an amphotericin ELISA of hydrogel discs, where multiple samples (n=9) were analysed, and also via the UV absorbance of a cross section of the hydrogel sheet where a distinct increased absorption for amphotericin was observed at 550 nm (see FIG. 9 and FIG. 10), and this increase could be correlated back to drug loading.

Hydrogel sheets were prepared (thickness=500 µm) by copolymerising GMMA, GME and EDMA using UV light. Then the epoxide group of GME was reacted with excess diamine to provide hydrogels with primary amine functionality. The primary amines were then reacted with Branched-PNIPAM-Amp with a fraction (~30%) of the end groups activated to amidation as the succimidyl ester and the rest of the end groups were functionalised with Amp-B groups. This created a clear hydrogel sheet with a smooth surface (see FIG. 2) that could be easily cut into discs. Table 4 provides the characterisation data of each of these hydrogels.

TABLE 4

Characterisation data of the prepared hydrogels

| Reference no. | Feed of Branched-PNIPAM-Amp | Amphotericin Functionality/ mol g$^{-1}$ | Water content/ wt % |
|---|---|---|---|
| Branched-PNIPAM* | 30* | 0 | 59% |
| Branched-PNIPAM-Amp | 60* | 100 µg mg$^{-1}$ | 60% |

Attachment of Organisms to Hydrogels
Interaction and Attachment of Organisms to Hydrogels with Single Functionalised Polymer in In-Vitro Experiments GMMA-hydrogels with linked Branched-PNIPAMs funtionalised with Amp-B were exposed to *C. albicans*. The functionalised surface with grafted Branched-PNIPAM-Amp was shown to bind the microbial species both effectively and selectively.

*C. albicans* was incubated in vitro with amphotericin functionalised GMMA-hydrogel for 1 hour. Hydrogels were washed 3× PBS and imaged using a fluorescence microscope. 8 fields of view were imaged and the number of organisms attaching to the hydrogels per field of view (see FIG. 8) were analysed using Image J. The number of organisms attaching to the functionalised hydrogels was compared with a non-functionalised hydrogel Bars indicate mean±SEM of 8 fields of view analysed from at least 3 independent experiments Representative examples of images of *C. albicans* attached to the surface of the functionalised hydrogel are shown in FIG. 8.

While specific embodiments of the invention have been described for the purpose of reference and illustration, various modifications will be apparent to a person skilled in the art without departing from the scope of the invention as defined by the appended claims.

REFERENCES

[1] A. Casadevall, *Health Security* 2017, 15, 341-342.
[2] M. Bassetti and E. Righi, *Seminars in Respiratory and Critical Care Medicine* 2015, 36, 796-806.
[3] D. W. Denning, *Philosophical Transactions of the Royal Society B: Biological Sciences* 2016, 371.
[4] J. Sengupta, A. Khetan, S. Saha, D. Banerjee, N. Gangopadhyay and D. Pal, *Cornea* 2012, 31, 371-375.
[5] P. D. H. Feldmann in *Yeast Cell Architecture and Functions*, Wiley-VCH Verlag GmbH & Co. KGaA, 2012, pp. 5-24.
[6] K. C. Gray, D. S. Palacios, I. Dailey, M. M. Endo, B. E. Uno, B. C. Wilcock and M. D. Burke, *Proceedings of the National Academy of Sciences* 2012, 109, 2234-2239.
[7] J. Brajtburg, W. G. Powderly, G. S. Kobayashi and G. Medoff, *Antimicrobial Agents and Chemotherapy* 1990, 34, 183-188.
[8] L. Storm, K. R. Lausch, M. C. Arendrup, K. L. Mortensen and E. Petersen, *Medical Mycology Case Reports* 2014, 6, 6-9.
[9] A. Wong-Beringer, R. A. Jacobs and B. J. Guglielmo, *Clinical Infectious Diseases* 1998, 27, 603-618.
[10] a) L. Jaimes-Aguirre, B. V. Gibbens-Bandala, E. Morales-Avila, B. E. Ocampo-Garcia, M. Seyedeh-Fatemeh and A. Amirhosein, *Current Pharmaceutical Design* 2016, 22, 2886-2903; b) T. C. M. M. Carraro, N. M. Khalil and R. M. Mainardes, *Pharmaceutical Development and Technology* 2016, 21, 140-146.
[11] a) P. Jansook, W. Pichayakorn, C. Muankaew and T. Loftsson, *Drug Development and Industrial Pharmacy* 2016, 42, 1446-1454; b) C. Alvarez, D. H. Shin and G. S. Kwon, *Pharmaceutical Research* 2016, 1-9.
[12] a) A. Halperin, Y. Shadkchan, E. Pisarevsky, A. M. Szpilman, H. Sandovsky, N. Osherov and I. Benhar, *Journal of Medicinal Chemistry* 2016, 59, 1197-1206; b) T. R. M. Tan, K. M. Hoi, P. Zhang and S. K. Ng, *PLoS ONE* 2016, 11, e0152112.
[13] a) V. Janout, W. A. Schell, D. Thevenin, Y. Yu, J. R. Perfect and S. L. Regen, *Bioconjugate Chemistry* 2015, 26, 2021-2024; b) D. E. Ickowicz, S. Farber, E. Sionov, S. Kagan, A. Hoffman, I. Polacheck and A. J. Domb, *Biomacromolecules* 2014, 15, 2079-2089.
[14] S. Rimmer, S. Carter, R. Rutkaite, J. W. Haycock, L. Swanson, *Soft Matter,* 2007, 3, 971
[15] R. Espada, J. M. Josa, S. Valdespina, M. A. Dea, M. P. Ballesteros, J. M. Alunda, J. J. Torrado *Biomed Chromat* 2008, 22, 402
[16] R. A. Cordeiro, C. E. C. Teixeira, R. S. N. Brilhante, D. S. C. M. Castelo-branco, M. A. N. Paiva, J. J. Giffoni Leite, D. T. Lima, A. J. Monteiro, J. J C. Sidrim, M. F. G. Rocha, *Medical Mycology* 2013, 51, 53
[17] P. Teratanatorn, R. Hoskins, T. Swift, C. W. I. Douglas, J. Shepherd and S. Rimmer, *Biomacromolecules* 2017.
[18] T. Swift, R. Hoskins, R. Telford, R. Plenderleith, D. Pownall and S. Rimmer, *Journal of Chromatography A* 2017, 1508, 16-23.
[19] T. Swift, J. Lapworth, K. Swindells, L. Swanson and S. Rimmer, *RSC Advances* 2016, 6, 71345-71350.
[20] D. Al-Badriyeh, C. F. Neoh, K. Stewart and D. C. M. Kong in *Clinical utility of voriconazole eye drops in ophthalmic fungal keratitis*, Vol. 4 2010, pp. 391-405.
[21] A. Lemke, A. F. Kiderlen and O. Kayser, *Applied Microbiology and Biotechnology* 2005, 68, 151-162.

[22] P. Deshpande, M. Notara, N. Bullett, J. T. Daniels, D. B. Haddow and S. MacNeil, *Tissue Engineering Part A* 2009, 15, 2889-2902.
[23] R. Plenderleith, T. Swift and S. Rimmer, *RSC Advances* 2014, 4, 50932-50937.

The invention claimed is:

1. A polymer conjugate, or a salt thereof, having the general formula:

$P-[Q]_x$ wherein:
P is a branched temperature-responsive polymer comprising a plurality of functional groups, wherein one or more of said functional groups are covalently attached to a ligand capable of binding to ergosterol;
Q is a ligand capable of binding to ergosterol; and
x is the percentage of functional groups on the branched temperature-responsive polymer, P, that are attached to Q, wherein x is greater than or equal to 10%,
wherein the branched temperature-responsive polymer, P, is branched poly(N-isopropylacrylamide); and the ligand capable of binding to ergosterol, Q, is amphotericin B, nystatin or natamycin; and
wherein each ligand capable of binding to ergosterol, Q, present in the polymer conjugate is bound to a terminus of one of the branches of the branched temperature-responsive polymer, P, by the reaction of a carboxyl group present on the branched temperature-responsive polymer, P, with an amine group present on the ligand capable of binding to ergosterol, Q, to form a —C(O)—NH-linking group.

2. A polymer conjugate according to claim 1, or a salt thereof, wherein x is greater than or equal to 50%.

3. A polymer conjugate according to claim 1, or a salt thereof, wherein the branched temperature-responsive polymer, P is a temperature-responsive polymer having branches occurring at every 15 to 25 monomer units.

4. A polymer conjugate according to claim 1, or a salt thereof, wherein the branched temperature-responsive polymer, P, is formed from: a) N-isopropylacrylamide; and b) one or more branching agents selected from 4-vinylbenzyl-pyrrolecarbodithioate (VPC), vinylbenzyl-phenylcarbodithioate, vinylbenzyl imidazoledithioate, vinylbenzyl alkyldithoates, and derivatives thereof.

5. A polymer conjugate according to claim 4, or a salt thereof, wherein the branching agent is 4-vinylbenzyl-pyrrolecarbodithioate (VPC).

6. A polymer conjugate according to claim 4, or a salt thereof, wherein the molar ratio of temperature responsive monomer to branching agent is within a range of 40:1 to 15:1.

7. A polymer conjugate according to claim 1, or a salt thereof, wherein the ligand capable of binding to ergosterol, Q, is amphotericin B.

8. A polymer conjugate according to claim 1, or a salt thereof, wherein the polymer conjugate has the formula:

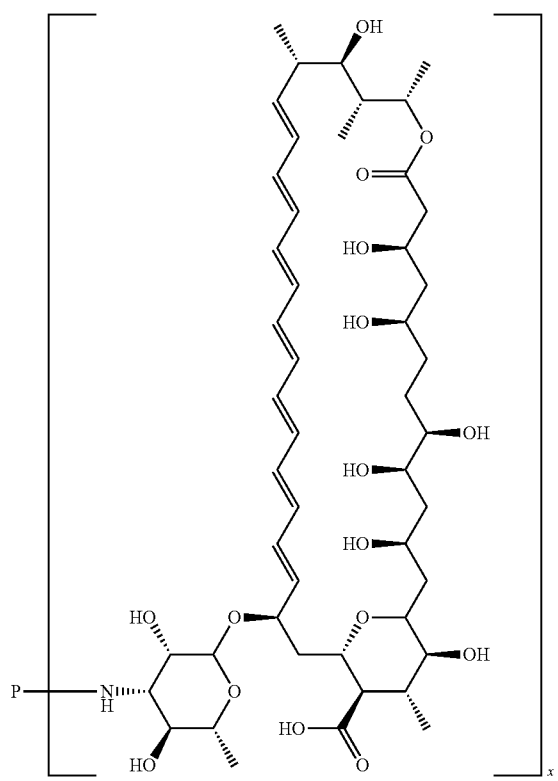

wherein the group in the square brackets is amphotericin B, P is the branched temperature-responsive polymer and x is the percentage of terminal functional groups of the branched temperature-responsive polymer, P, that are attached to amphotericin B, wherein x is greater than or equal to 50%.

9. A polymer conjugate according to claim 8, or a salt thereof, wherein:
P is a branched poly(N-isopropylacrylamide) comprising:
a) a plurality of terminal carboxyl groups; and
b) between 0.01 and 20 mole percent of a 4-vinylbenzyl-pyrrolecarbodithioate (VPC) branching agent;
each amphotericin B molecule is covalently attached to a terminal carboxyl group of the branched temperature-responsive polymer, P, via its amino group, so as to form a direct linkage in the form of an amide bond; and
at least 80% of the total terminal carboxyl groups present on the branched temperature-responsive polymer are attached to an amphotericin B molecule.

10. A hydrogel composition comprising a hydrogel matrix, an aqueous medium and a polymer conjugate according to claim 1, or a salt thereof, dispersed within the hydrogel.

11. A hydrogel composition according to claim 10, wherein the polymer conjugate, or a salt thereof, is bound to the hydrogel matrix.

12. A hydrogel composition according to claim 10, wherein the water content of the hydrogel is greater than 70% w/w.

13. A contact lens, membrane, swab or wound dressing comprising a hydrogel composition according to claim 10.

* * * * *